United States Patent [19]

Sumitani et al.

[11] Patent Number: 4,695,667
[45] Date of Patent: Sep. 22, 1987

[54] NOVEL CRYSTALLINE ALUMINOSILICATE ZEOLITES AND PROCESS FOR PRODUCTION THEREOF

[75] Inventors: Koji Sumitani; Tokuji Sakai; Yasuo Yamasaki; Tamio Onodera, all of Matsuyama, Japan

[73] Assignee: Teijin Petrochemical Industries, Ltd., Tokyo, Japan

[21] Appl. No.: 705,631

[22] Filed: Feb. 26, 1985

Related U.S. Application Data

[62] Division of Ser. No. 634,449, Jul. 25, 1984, which is a division of Ser. No. 317,918, Nov. 3, 1981, abandoned.

[30] Foreign Application Priority Data

Nov. 4, 1980 [JP] Japan ................................. 55-155017
Mar. 6, 1981 [JP] Japan ................................. 56-31182
Jun. 10, 1981 [JP] Japan ................................. 56-88024
Jul. 20, 1981 [JP] Japan ................................. 56-112264

[51] Int. Cl.$^4$ ............................................... C07C 5/27
[52] U.S. Cl. ..................................................... 585/481
[58] Field of Search ................................. 585/481, 480

[56] References Cited

U.S. PATENT DOCUMENTS 3,409,686 11/1968 Mitsch .................................. 585/481
4,537,754 8/1985 Cafri et al. ........................... 423/277

FOREIGN PATENT DOCUMENTS 1566011 3/1969 France ................................. 585/481
9041324 8/1972 Japan ................................... 585/481
8121224 1/1982 Japan ................................... 585/481

Primary Examiner—Asok Pal
Attorney, Agent, or Firm—Sherman and Shalloway

[57] ABSTRACT

A novel crystalline aluminosilicate zeolite characterized by having a composition of the following general formula expressed in terms of the mole ratios of oxides in the anhydrous state $$xM_{2/n}O \cdot Al_2O_3 \cdot ySiO_2$$

wherein M represents at least one cation having a valence of n, x is a number between 0.5 and 4, and y is a number of at least 10, and having a specific X-ray diffraction pattern. Said crystalline aluminosilicate zeolite can be produced by maintaining a mixture of a water-soluble alkali metal compound, an N,N,N,N',N',N'-hexamethyl-1,6-hexane diammonium compound, a compound capable of giving silica under the reaction conditions, a compound capable of giving alumina under the reaction conditions and water, at a temperature of at least 80° C. for a period sufficient to form crystals, and is useful as a catalyst for, for example, transalkylation or alkylation reaction of toluene, isomerization of xylene, isomerization of ethylbenzene to xylenes, etc.

12 Claims, 9 Drawing Figures

NOVEL CRYSTALLINE ALUMINOSILICATE ZEOLITES AND PROCESS FOR PRODUCTION THEREOF

This is a division of application Ser. No. 634,449, filed July 25, 1984, which in turn is a division of application Ser. No. 317,918 filed Nov. 3, 1981, now abandoned.

This invention relates to novel crystalline aluminosilicate zeolites, and more specifically, to novel crystalline aluminosilicate zeolites having a different crystalline structure from any of hitherto known crystalline aluminosilicate zeolites, a process for the production thereof, and used thereof as a catalyst.

In the present specification and the appended claims, the crystalline aluminosilicate zeolites are referred to simply as "zeolites" unless otherwise specified.

Zeolites, whether naturally occurring or synthetic, are characterized by containing cations such as Na, K or hydrogen ion and having a three-dimensional network structure composed mainly of $SiO_4$ and $AlO_4$ and a highly oriented structure of tetrahedrons of Si atoms and Al atoms interconnected through oxygen atoms. The zeolites have a number of pores of uniform size, and by utilizing these pores, they find wide applications as molecular sieves and catalysts or carriers in various chemical syntheses.

Because synthetic zeolites are very homogeneous and have a high purity and excellent properties, numerous synthetic zeolites and processes for their production have been suggested in the past.

Zeolites having a high silica content, for example those with an $SiO_2/Al_2O_3$ mole ratio of at least 10, have high stability and unique acidity, and possess selective adsorptive ability and high catalytic activity in the cracking, hydrocracking, isomerization, alkylation and other conversion reactions of hydrocarbons. A number of such high-silica zeolites, typified by ZSM-series zeolites, have been proposed to date.

The zeolites having a high silica content are usually produced by the reaction of a silica source and an alumina source with a combination of alkali metal cations and other cations, and the structures and properties of the resulting zeolites differ depending upon the type of the other cations and its combination with the alkali metal cations.

Examples of known cations to be used in combination with the alkali metal cations include specified quaternary ammonium compounds (for example, U.S. Pat. No. 3,965,207 and DT-AS No. 2548695), primary amines having 2 to 10 carbon atoms (U.S. Pat. No. 4,151,189), and alkyldiamines having 2 to 20 carbon atoms (U.S. Pat. No. 4,139,600).

It has now been found in accordance with this invention that the use of a specified quaternary ammonium ion in combination with an alkali metal cation leads to zeolites having quite a different crystalline structure from known zeolites, and that these zeolites are thermally stable and have a high purity and excellent catalytic activity in the conversion of certain hydrocarbons.

According to this invention, there is provided a crystalline aluminosilicate zeolite characterized by having a composition of the following general formula, expressed in terms of mole ratios of oxides in the anhydrous state

  (I)

wherein M represents at least one cation having a valence of n, x is a number between 0.5 and 4, and y is a number of at least 10, and having an X-ray diffraction pattern which shows at least the following significant peaks:

| Interplanar spacing d(Å) | Relative intensity |
|---|---|
| 11.2 ± 0.5 | medium to strong |
| 9.9 ± 0.5 | medium to strong |
| 4.67 ± 0.1 | medium |
| 4.33 ± 0.1 | very strong |
| 4.02 ± 0.05 | strong to very strong |
| 3.83 ± 0.05 | medium |
| 3.72 ± 0.05 | weak to medium |
| 3.44 ± 0.04 | weak to strong |
| 3.33 ± 0.04 | weak to strong |
| 3.28 ± 0.03 | medium |

The zeolites provided by this invention have a high silica content represented by an $SiO_2/Al_2O_3$ mole ratio of at least 10, but have a novel crystalline structure showing quite a different X-ray diffraction pattern from conventional high-silica zeolites, for example ZSM-series zeolites such as ZSM-5, ZSM-11, ZSM-12 and ZSM-38 and Zeta 3 zeolites. The zeolites of the invention are termed "zeolites TPZ-3" in the present application.

The properties of zeolites TPZ-3 of this invention and their manufacturing process will be described below in detail with reference to the accompanying drawings.

Figure 1:
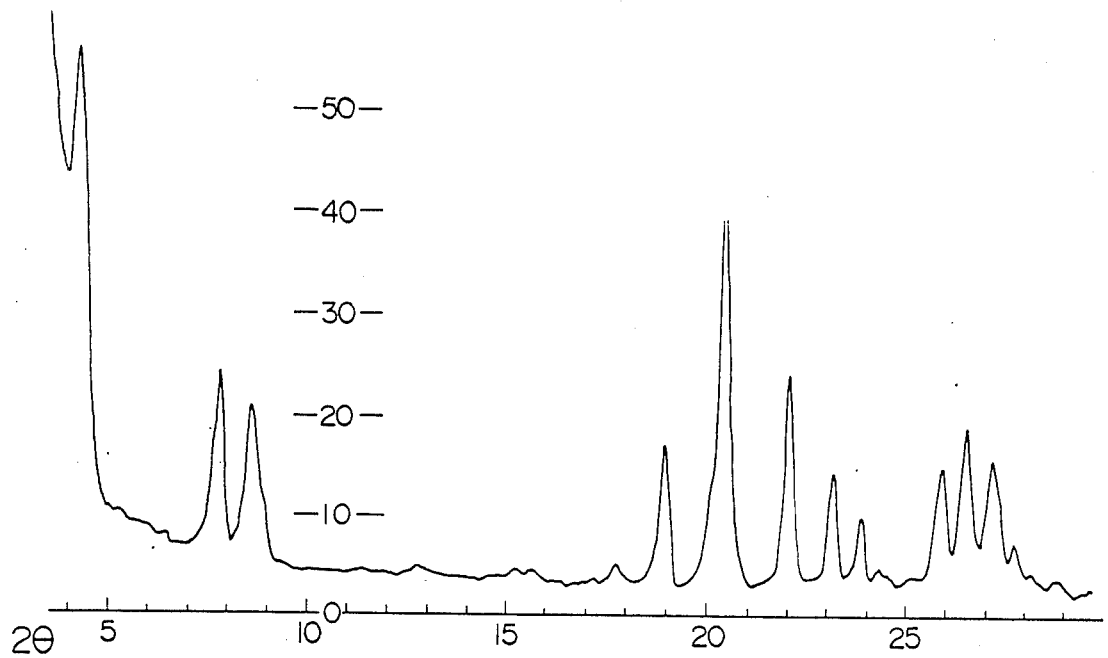
FIGS. 1-7 are plots of the X-ray diffraction data for the zeolite products of Example 1-7, respectively.

According to this invention, the zeolite TPZ-3 can be produced by maintaining a mixture containing a water-soluble alkali metal compound, an N,N,N,N',N',N',-hexamethyl-1,6-hexane diammonium compound, a compound capable of giving silica under the reaction conditions (the hydrothermal reaction conditions to be described hereinbelow) (to be referred to as a silica source), a compound capable of giving alumina under the reaction conditions (under the hydrothermal reaction conditions to be described below) (to be referred to as an alumina source) and water at a temperature of at least 80° C. for a period sufficient to form crystals, and as required, subjecting the resulting zeolite to ion-exhange reaction with another cation.

The essential characteristic feature of the process of this invention consists in the use of an N,N,N,N',N',N'-hexamethyl-1,6-hexane diammonium compound as a cation source constituting the cation portion of the zeolite in addition to a water-soluble alkali metal compound.

In the process of this invention, the starting compounds are mixed in such proportions that the mole ratios of the individual elements in the resulting mixture are as follows:

$SiO_2/Al_2O_3 = 10-2{,}000$, preferably 10–500, more preferably 20–250;

$R/(Si+Al) = 1 \times 10^{-4} - 1$, preferably $5 \times 10^{-4} - 0.05$, more preferably $1 \times 10^{-3} - 1 \times 10^{-1}$;

$OH^-/(Si+Al) = 1 \times 10^{-4} - 1.5$, preferably $1 \times 10^{-3} - 1$, more preferably $5 \times 10^{-3} - 0.4$;

$H_2O/(Si+Al)=5-100$, preferably 10-50, more preferably 15-40;

$OH^-/H_2O=1\times 10^{-5}-1\times 10^{-1}$, preferably $1\times 10^{-4}-1\times 10^{-1}$, more preferably $1\times 10^{-4}-1\times 10^{-2}$ R represents an N,N,N,N',N',N'-hexamethyl-1,6-hexane diammonium ion, $[(CH_3)_3N^\oplus-CH_2)_6N^\oplus(CH_3)_3]$.

In the above formula, $OH^-$ represents the degree of alkalinity of the mixture quantitatively, which is calculated by subtracting the molar proportion of the hydroxyl groups consumed by neutralization with acid radicals in the reaction mixture from the total molar proportion of the hydroxyl groups carried over the mixture by the starting compounds other than water.

These starting compounds will be described in greater detail below.

(A) The silica source used in this invention may be any silica sources which are normally used in the production of zeolites, for example powdery silicas, colloidal silicas, soluble silicates, and silicic acid. Suitable powdery silicas are, for example, precipitated silicas produced from alkali metal silicates by the precipitation method, such as aerosol silica, fuming silica and silica gel. Colloidal silicas may be in various particle sizes, for example 10 to 50 microns. Examples of the soluble silicates are water glass containing 1 mole of $Na_2O$ or $K_2O$ and 1 to 5 moles, particularly 2 to 4 moles, of $SiO_2$, and alkali metal silicates. Colloidal silica and water glass are especially preferred as the silica source.

(B) The alumina source used in this invention may be any alumina sources which are generally used in the production of zeolites. Examples include aluminum salts such as its chloride, nitrate and sulfate; hydrated alumina or alumina capable of being hydrated, such as colloidal alumina, pseudoboehmite, boehmite, γ-alumina, α-alumina, and β-alumina trihydrate and sodium aluminate. Sodium aluminate and aluminum salts are preferred as the alumina source.

It is also possible to use aluminosilicate salts, such as naturally occurring feldspar, kaolinite, acid clay, bentonite and montmorillonite as sources of both silica and alumina. These aluminosilicates may be substituted for a part or the whole of the aforesaid alumina source and/or silica source.

The mixing ratio of the silica source and the alumina source in the starting mixture used in this invention, as the $SiO_2/Al_2O_3$ mole ratio, is from 10 to 2,000 preferably from 10 to 500, especially preferably from 20 to 250.

(C) Water-soluble alkali metal salts and alkali metal hydroxides are suitable as the water-soluble alkali metal compounds. Specific examples are the chlorides and carbonates of alkali metals, such as sodium chloride, potassium chloride, sodium carbonate, and potassium carbonate, and alkali metal hydroxides such as sodium hydroxide and potassium hydroxide.

Alkali metal silicates such as sodium silicate and potassium silicate and alkali metal aluminates such as sodium aluminate and potassium aluminate may also be used as sources of both silica and alumina.

Especially suitable alkali metal compounds are sodium hydroxide, sodium silicate and sodium aluminate.

(D) The N,N,N,N',N',N'-hexamethyl-1,6-hexane diammonium compound used together with the water-soluble alkali metal compound is a compound expressed by the following formula

$Y^\ominus.(CH_3)N^\oplus-(CH_2)_6N^\oplus(CH_3)_3.Y^\oplus$ wherein $Y^-$ represents an anion such as a halogen ion, an $OH^-$ ion or a $\frac{1}{2}SO_4^{--}$ ion. This compound as such may be mixed with the other starting compounds, or it may be formed in situ in the mixture by reacting N,N,N',N'-tetramethyl-1,6-hexanediamine with a methyl halide such as methyl iodide.

The diammonium compound may be used in an amount of $1\times 10^{-4}$ to 1 mole, preferably $5\times 10^{-4}$ to 0.5 mole, especially preferably $1\times 10^{-3}$ to $1\times 10^{-1}$ mole, per mole of Si plus Al in the silica source and the alumina source.

In the starting mixture used in the process of this invention, the presence of the $OH^-$ ion in an amount above a certain value is necessary. Accordingly, at least one of the starting compounds other than water should dissociate an $OH^-$ ion. Usually, the $OH^-$ ion is supplied to the mixture by the aforesaid alkali metal compound and/or diammonium compound.

The $OH^-$ ion may be present in an amount of $1\times 10^{-4}$ to 1.5 moles, preferably $1\times 10^{-3}$ to 1 mole, especially preferably $5\times 10^{-3}$ to 0.4 mole, per mole of Si plus Al in the silica source and the alumina source.

Furthermore, the $OH^-$ ion may be present in an amount of $1\times 10^{-5}$ to $1\times 10^{-1}$ mole, preferably $1\times 10^{-4}$ to $1\times 10^{-1}$ mole, especially preferably $1\times 10^{-4}$ to $1\times 10^{-2}$ mole, per mole of water in the mixture.

(E) In the starting mixture used in this invention, the use of water in an amount of 5 to 100 moles, preferably 10 to 50 moles, especially preferably 15 to 40 moles, per mole of (Si+Al) brings about favorable results.

According to this invention, the desired zeolite can be formed by mixing the aforesaid alkali metal compound N,N,N,N',N',N'-hexamethyl-1,6-hexane diammonium compound, silica source, alumina source and water in the proportions described above, and maintaining the resulting mixture at a temperature and for a period sufficient to form the zeolite (i.e., subjecting the mixture to hydrothermal reaction). The reaction temperature is at least 80° C., advantageously 100° to 200° C. The reaction period is usually 5 hours to 100 days, preferably 10 hours to 50 days, especially preferably 1 day to 7 days. The pressure is the autogenous pressure of the system to a higher pressure. Generally, the reaction is carried out in an autoclave under autogenous pressure. As required, it may be carried out in an atmosphere of an inert gas such as nitrogen gas.

The reaction of forming the zeolite is carried out by heating the starting mixture to a desired temperature, if desired with stirring, until the zeolite is formed. After the crystals are formed, the reaction mixture is cooled to room temperature, filtered, and washed fully with water preferably until the washing has an electric conductivity of generally not more than 50 μ /cm, preferably not more than 25 μ /cm, especially preferably not more than 15 μ /cm. If desired, the product is then dried. Zeolites may be carried out at room temperature or at an elevated temperature of up to about 150° C. The drying may be carried out under atmospheric or reduced pressure. Preferably, it is carried out, for example, at about 50° to about 130° C. under atmospheric pressure for about 5 to 24 hours.

It has been found that the presence of fine particles of the desired zeolite TPZ-3 in the starting mixture for the aforesaid zeolite-forming reaction may sometimes increase the rate of the zeolite-forming reaction. Thus, the inclusion of a small amount of the fine particles of the desired zeolite TPZ-3 as a seed in the starting mixture frequently brings about favorable results.

A quaternary ammonium compound and/or a water-soluble amine having a lower molecular weight than the diammonium compound may be added to the starting mixture. This can increase the rate of the zeolite-forming reaction. Examples of the quaternary ammonium compounds used for this purpose are tetramethyl ammonium chloride and tetraethyl ammonium chloride. The amine or the ammonium compound may be added in an amount of generally 0.1 to 10 moles, preferably 0.1 to 5 moles, per mole of the N,N,N,N′,N′.N′-hexamethyl-1,6-hexane diammonium compound.

The resulting zeolite TPZ-3 contains an alkali metal ion and an N,N,N,N′,N′,N′-hexamethyl-1,6-hexane diammonium ion as cations. The cation sites of the zeolite TPZ-3 may be replaced by an ammonium ion by the action of, for example, an aqueous solution of ammonium chloride.

The resulting zeolites may be calcined at a temperature of about 100° to about 600° C., preferably about 300° to about 500° C., for a period of about 8 hours to about 24 hours, preferably about 8 hours to about 16 hours. This calcination procedure can result in the removal of an organic cation and/or an ammonium ion at the cation sites, and consequently, zeolite TPZ-3 in which the cation sites consist substantially of an alkali metal ion and/or a hydrogen ion can be obtained.

Furthermore, according to this invention, at least a part of the cations present in the cation sites may be exchanged with another cation by subjecting the cation sites of the resulting zeolite TPZ-3 with said other cation.

The cation exchange reaction can be carried out by methods known per se. Exchangeable cations are any of those which can be present as cations in a medium in which the cation exchange reaction is carried out. They include metal cations which are usually employed in the ion-exchanging of zeolites. Specifically, they include cations of metals of Groups I, II, III and VIII of the periodic table. Examples include lithium, sodium, potassium, rubidium, cesium, copper, silver, beryllium, magnesium, calcium, strontium, barium, zinc, cadmium, mercury, scandium, yttrium, lanthanum, cerium, proseodymium, neodymium, promethium, samarium, europium, gadolinium, terbium, dysprosium, holmium, erbium, thulium, ytterbium, lutetium, iron, cobalt, nickel, ruthenium, rhodium, palladium, osmium, iridium, and platinum.

Of these, the cation of metals of Groups IA (alkali metals), IIA (alkaline earth metals) and IIIB (rare earth metals) are preferred.

The exchange reaction with these cations may be carried out by methods known per se, for example by contacting the zeolite with an aqueous solution containing the desired cation. The contacting treatment may be effected batchwise or continuously. The crystallinity or activity of the zeolite TPZ-3 of the invention can sometimes be increased by performing this ion exchange.

The zeolite TPZ-3 produced in the above manner has a characteristic X-ray diffraction pattern, and can be clearly distinguished from conventional zeolites having a high silica content in that it has at least the following significant peaks.

| Interplanar spacing d(Å) | Relative intensity |
|---|---|
| 11.2 ± 0.5 | medium to strong |

-continued

| Interplanar spacing d(Å) | Relative intensity |
|---|---|
| 9.9 ± 0.5 | medium to strong |
| 4.67 ± 0.1 | medium |
| 4.33 ± 0.1 | very strong |
| 4.02 ± 0.05 | strong to very strong |
| 3.83 ± 0.05 | medium |
| 3.72 ± 0.05 | weak to medium |
| 3.44 ± 0.04 | weak to strong |
| 3.33 ± 0.04 | weak to strong |
| 3.28 ± 0.03 | medium |

For example, a very strong peak is observed at 4.33±0.1 Å in the zeolite TPZ-3 of the invention, whereas such a peak is not seen in known ZSM-5 zeolite. It is further noted that while a strong peak is seen at 4.02±0.05 Å in the zeolite TPZ-3 of the invention, only a relatively weak peak exists at 4.02±0.05 Å in zeolite ZSM-12.

It should be understood that these characteristic peaks of X-ray lattice interplanar spacings are common to all zeolite TPZ-3 species of the invention although there may be some minor shifts in interplanar spacing and/or some variations in relative intensity depending upon the type of the cation M in formula (I) which shows the chemical composition of the zeolites TPZ-3 of the invention.

The values of interplanar spacings d (Å) in the X-ray diffraction pattern, as described in the present specification and the appended claims, are determined by standard techniques. Specifically, the radiation is the K-alpha doublet of copper, and a scintillation counter spectrometer with a strip chart pen recorder is used. The peak heights (I) and 2θ (θ is the Bragg angle) are read from the spectrometer chart. From these, the relative intensities, $100 \times I/I_o$ (in which $I_o$ is the intensity of the strongest line or peak) and d, the interplanar spacing in Å corresponding to the recorded lines, are calculated.

The relative intensity is the ratio of the height of a given peak to the height of a peak at an interplanar spacing d of 4.33±0.1 Å which is taken as 100, and it is expressed on the following standards.

| Relative intensity | Expression |
|---|---|
| 100–60 | very strong |
| 60–40 | strong |
| 40–20 | medium |
| 20–10 | weak |

It should be understood that the zeolites TPZ-3 of this invention include all zeolites TPZ-3 having the above characteristic peaks of X-ray lattice interplanar spacings irrespective of whether peaks exist at other places. Sometimes, the X-ray diffraction pattern of the zeolites TPZ-3 of the invention shows a strong peak in the vicinity of 20 Å in addition to the aforesaid characteristic peaks, but the presence or absence of this peak does not substantially affect the identification of the zeolites TPZ-3 of the invention.

Chemically, the zeolites TPZ-3 of the invention have a composition of the following general formula, expressed in terms of mole ratios of oxides in the anhydrous state.

$$xM_{2/n}O \cdot Al_2O_3 \cdot ySiO_2 \tag{I}$$

wherein M, n, x and y are as defined hereinabove.

In formula (I), x is an index of the amount of the cations bonded to the zeolite. In the zeolites TPZ-3 of the invention, x is within the range of 0.5 to 4, preferably 0.9 to 3.

In a model system, zeolite, i.e. a crystalline aluminosilicate, is basically composed of an interconnected structure of tetrahedrons of silica and tetrahedrons of alumina.

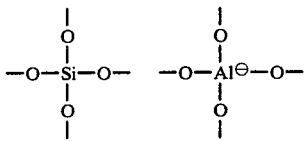

The charges of the alumina tetrahedrons are neutralized as a result of incorporation of cations in the crystals. Accordingly, "x" which represents the amount of cations in formula (I) is theoretically equimolar to alumina, namely 1. In practice, however, it is usual that the synthesized zeolite includes a cation precursor which cannot be completely removed by usual washing operations, and actual analytical data of the synthetic zeolites scarcely show x to be 1. It should be understood therefore that "x" in formula (I) represents the amount (in moles) of total cations in a purified synthetic zeolite including a cation of a cation precursor which cannot be completely removed by usual washing operations.

On the other hand, y which is an index of the silica content of the zeolite, is at least 10, preferably 10 to 2,000, especially preferably 10 to 500. Zeolites of formula (I) in which y is 20 to 250 have been found to have especially superior properties.

M in formula (I) which occupies the cation site of the zeolite of this invention is a cation having a valence of n. Specific examples of M are a hydrogen ion, an ammonium ion, an organic cation and a metal cation. Examples of the organic cations are those added at the time of synthesizing zeolite TPZ-3, such as a N,N,N,N',N',N'-hexamethyl-1,6-hexane diammonium cation, a tetraethyl ammonium cation and a tetramethyl ammonium cation.

Examples of the metal cation are those given hereinabove with regard to the ion exchange reaction of the zeolite of this invention.

A hydrogen ion and metal cations are preferred as M in formula (I). Cations of metals of Groups I, II, III and VIII of the periodic table, especially those cations of metals of Groups IA, IIA and IIIB of the periodic table, are especially preferred. From the standpoint of end uses of the zeolite, ions of Group VIII metals, above all a platinum ion, are favorably used in this invention.

One characteristic property of the zeolite TPZ-3 of the invention is shape selectivity which can be expressed by the cyclohexane/n-hexane sorption ratio. This sorption ratio indicates the pore dimension of pores present in the zeolite, and denotes the ratio of the weight of cyclohexane adsorbed per unit weight of the zeolite to that of n-hexane adsorbed per unit weight of zeolite, the adsorption being effected at a certain fixed temperature and pressure. Low cyclohexane/n-hexane sorption ratios mean that molecules having a large cross-sectional area, such as cyclohexane molecules, have difficulty diffusing into the pores of the zeolite, and from the viewpoint of a catalytic reaction, lead to increased selectivity. The amount of cyclohexane or n-hexane adsorbed per unit weight of the zeolite can be determined by weighing a certain fixed amount of the zeolite dried by calcination in an electric furnace at 450° C. for 8 hours, then maintaining the weighed zeolite for 6 hours in a saturated gas atmosphere of cyclohexane or n-hexane at 25° C. and 120±20 mmHg, further maintaining the zeolite for 2 hours at 25° C. and 120±20 mmHg in the absence of cyclohexane or n-hexane, then weighing the zeolite having cyclohexane or n-hexane adsorbed thereto, and calculating the difference between the weight of the zeolite before the adsorbing operation and that after the adosrbing operation.

The zeolite TPZ-3 of this invention has a cyclohexane/n-hexane sorption ratio of generally not more than 0.95, preferably from 0.1 to 0.95, more preferably from 0.2 to 0.90.

The zeolite TPZ-3 of the invention is also characterized by the fact that it has much superior cracking activity to commercially available highly active silica-alumina cracking catalysts.

The cracking activity is expressed by the "cracking index" which represents a temperature that gives a certain fixed reaction velocity constant in the cracking reaction of hexanes. Specifically, it is measured as follows:

A zeolite or silica-alumina catalyst molded to a size of 10 to 20 mesh is calcined in the air at 450° C. for 8 hours, and then packed into a Pyrex glass tube reactor. Then, nitrogen gas saturated with hexanes at 25° C. is fed into the reactor, and the conversion of hexanes is measured. The reaction rate constant at each of the reaction temperature is calculated from the conversion. A reaction temperatyre at which the reaction rate constant becomes 0.5 is presumed, and is defined as the cracking index (°C.).

The cracking index of the zeolite TPZ-3 of the invention differs depending upon the type and amount of a cation which exists in the cation site. To cite typical examples, the zeolite TPZ-3 of the invention has a cracking index of not more than 300 when the cation is a hydrogen ion; about 300 when the cation is a beryllium ion (BeO/Al$_2$O$_3$ mole ratio=0.97); and 400 when the cation is a strontium ion (SrO/Al$_2$O$_3$ mole ratio=0.95). In regard to the amount of the cation introduced into the cation site, the cracking index of the zeolite TPZ-3 containing a sodium ion is about 300 when the Na$_2$O/Al$_2$O$_3$ mole ratio is 0.12, and about 400 when this mole ratio is 0.55.

The zeolite TPZ-3 of the invention has very good thermal stability. This can be demonstrated by the fact that when it is heat-treated at 800° C. for 12 hours or more, the X-ray diffraction pattern of the zeolite does not substantially change.

Because of the aforesaid excellent properties, the zeolite TPZ-3 of the invention can be used widely as a catalyst for the conversion reactions of aromatic hydrocarbons such as the disproportionation, isomerization, alkylation, transalkylation and dealkylation of alkylbenzenes, or as a selective adsrbent or as a catalyst carrier.

As a catalyst in these conversion reactions, the zeolite of the invention may be used as such. Depending upon the reaction to be catalyzed, it may also be used after supporting thereon a catalytically active metal or metal oxide which is identical or different with or from the metal cation present in the cation site. Examples of the catalytically active metals or metal oxides used for this purpose are iron, cobalt, nickel, copper, zinc, ruthenium, rhodium, palladium, rhenium, osmium, iridium and platinum, and the oxides of these.

Such a catalytically active metal or metal oxide may be deposited on the zeolite by methods known per se, for example, by the method described in European Patent Application Specification No. 0018498. Instead of depositing the catalytically active metal or metal oxide on the zeolite of the invention, it is also possible to deposit the metal or metal oxide on a conventional refractory oxide carrier, preferably alumina, mix the supported metal or metal oxide with the zeolite of the invention, mold the mixture into a desired shape such as pellets or tablets, and then use the molded product in the intended reaction.

Since the zeolite TPZ-3 of the invention can be advantageously used particularly in the disproportionation of toluene, the methylation of toluene, the isomerization of xylenes and the isomerization of ethylbenzene to xylenes, these reactions will be described below somewhat specifically.

In these reactions, the zeolite TPZ-3 of the invention may be used in the form of a fine powder, or as required, in the form of pellets, tablets and other desired shapes obtained by molding it in a usual manner. Molding of the zeolite TPZ-3 is carried out in a customary manner by mixing it with a synthetic or natural refractory inorganic oxide used ordinarily as a binder for zeolite catalysts, such as silica, alumina, silica-alumina, kaolin, or silica-magnesia, molding the mixture into the desired shape, and then calcining the molded product. Advantageously, the amount of the zeolite TPZ-3 in the molded product is generally 1 to 100% by weight, preferably 10 to 90% by weight, based on the weight of the molded product.

Prior to use, the catalyst so prepared may be treated at a temperature of 200° to 600° C., preferably 250° to 550° C., in a reducing atmosphere such as hydrogen gas.

(1) Disproportionation of toluene

Disproportionation of toluene is a reaction of forming xylenes by intramolecular methyl exchange of toluene itself and methyl exchange between toluene and a methyl exchanging agent. The disproportionation reaction of toluene can be advantageously carried out in the presence of the zeolite TPZ-3 provided by this invention.

Examples of the methyl exchanging agent are methylsubstituted benzenes, for example trimethylbenzenes such as 1,3,5-trimethylbenzene or 1,2,4-trimethylbenzene, and tetramethylbenzenes such as durene. The trimethylbenzenes are preferred.

The ratio between the methyl exchanging agent and toluene fed into the reaction system varies depending mainly upon the type of the methyl exchanging agent. Advantageously, the mole ratio of the former to the latter is generally from 0.05 to 3, preferably from 0.08 to 2.5.

The disproportionation reaction can be carried out at a temperature of generally 200° to 650° C., preferably 300° to 550° C. The zeolite TPZ-3 of the invention is characterized by having higher activity at relatively low temperature within this range than mordenite catalysts and ZSM-5 catalysts.

The catalytic reaction in the disporportionation of toluene is carried out at a weight hourly space velocity (WHSV) of 0.1 to 500 hr$^{-1}$, preferably 0.5 to 100 hr$^{-1}$, based on the TPZ-3 zeolite. WHSV is defined as the amount (g) of toluene or the total amount (g) of toluene and the methyl exchanging agent, which is or are contacted with the zeolite catalyst per gram of the zeolite per hour.

The disproportionation reaction can be carried out at a pressure of generally from atmospheric pressure to 200 kg/cm$^2$·G, preferably from 1 to 100 kg/cm$^2$·G. A diluent such as nitrogen or hydrogen may be supplied to the feedstock. Supplying of hydrogen is advantageous industrially because it will prolong the life of the catalyst activity. The suitable amount of hydrogen used in this case is 0.1 to 100 moles, preferably 1 to 50 moles, per mole of toluene or both toluene and the methyl exchanging agent.

In performing the disproportionation reaction, the contacting of the feed gas with the catalyst may be effected in a fixed bed or fluidized bed reactor. Preferably, the former is used.

According to the disproportionation reaction described above, an isomeric mixture of xylenes can be obtained at a high conversion of toluene to xylenes. Furthermore, the active lifetime of the catalyst is long, and the catalytic activity of the zeolite TPZ-3 can be maintained at relatively low temperatures. Hence, this is a very advantageous method for industrial practice.

(2) Methylation of toluene

The zeolite TPZ-3 provided by this invention can also be advantageously used as a catalyst in the production of xylenes by methylation of toluene in the gaseous phase.

Methylating agents which are generally used for the methylation of the ring carbons of aromatic hydrocarbons may be used in this reaction. Examples include methanol, methyl chloride, methyl bromide and dimethyl ether, the methanol and dimethyl ether being preferred. Advantageously, the methylating agent is used in an amount of 0.05 to 3 moles, preferably 0.1 to 1.5 moles, per mole of toluene. To inhibit side-reactions, toluene is used preferably in excess of the methylating agent.

The methylation reaction is advantageously carried out at a temperature of generally 200° to 650° C., especially 250° to 600° C. The reaction pressure may be reduced, atmospheric or elevated pressures. Usually, atmospheric pressure and elevated pressures are employed. For example, the reaction is carried out at 1 atm. to 100 kg/cm$^2$·G.

In the methylation reaction, toluene and the methylating agent are contacted with the zeolite catalyst in the gaseous phase at a WHSV of generally 0.1 to 500, preferably 0.5 to 400. WHSV herein is defined as the total amount (g) of toluene and the methylating agent contacted with the zeolite catalyst per gram of the zeolite per hour.

The methylation reaction can be practiced both a fixed bed or fluidized bed reactor.

A diluent such as nitrogen or hydrogen may be supplied to the starting material. Desirably, the reaction is carried out while feeding hydrogen. This serves to maintain the activity of the catalyst high for long periods of time. The amount of hydrogen used for this purpose is 0.1 to 100 moles, preferably 1 to 20 moles, per mole of toluene and the methylating agent combined.

According to the above method, the activity of the zeolite TPZ-3 catalyst is not appreciably reduced even on long-term use, and the conversion of toluene can be maintained at a high level.

The xylenes obtained by the above methylating reaction are a mixture of o-, m- and p-xylenes in which the proportion of o-xylene is the highest.

For use in this methylating reaction, the zeolite TPZ-3 catalyst may have deposited thereon magnesium oxide (MgO), antimony oxide ($Sb_2O_3$), etc.

(3) Isomerization of xylene

The zeolite TPZ-3 provided by this invention is also useful as a catalyst for isomerization of xylenes. This reaction can be effected by heating a feedstock composed of a xylene isomeric mixture in which the concentration of at least one xylene isomer is lower than the thermodynamically equilibrium concentration, in the gaseous phase in the presence of the zeolite TPZ-3 catalyst.

Advantageously, the feedstock used in this reaction is a xylene isomeric mixture in which the concentration of p-xylene is lower than the thermodynamically equilibrium concentration. The feedstock may be a mixture of p-xylene, m-xylene and o-xylene, or a mixture of these xylenes and ethylbenzene. The isomeric mixture is contacted with the zeolite TPZ-3 catalyst in the gaseous phase.

Hydrogen may be caused to be present in the starting mixture in the isomerization reaction. When an H-form zeolite TPZ-3 is used as the catalyst, satisfactory results can be obtained in the absence of hydrogen. Generally, however, the use of hydrogen is frequently preferred. The amount of hydrogen used is desirably 1 to 100 moles per mole of the feedstock.

The above isomerization reaction may also be carried out in the presence of a non-aromatic hydrocarbon, particularly a non-aromatic hydrocarbon having a boiling point at atmospheric pressure of 50° to 150° C., especially 120° to 150° C., such as ethylcyclohexane, alkyl-substituted cyclopentanes, cyclohexanes, paraffin and naphthene.

The isomerization reaction is suitably carried out at a reaction temperature of generally 280° to 500° C., preferably 300° to 450° C., so that the weight hourly space velocity (WHSV) is adjusted generally to 0.1 to 200, preferably to 0.1 to 50.

The reaction pressure is desirably from atmospheric pressure to 30 kg/cm$^2$·G, preferably from atmospheric pressure to 25 kg/cm$^2$·G.

According to the isomerization reaction described above, a xylene mixture having a very high p-xylene approach to equilibrium can be obtained, and the active lifetime of the catalyst is long. Thus, p-xylene can be advantageously produced industrially.

By using the zeolite TPZ-3 catalyst, there was observed the unique phenomenon that under atmospheric pressure without using a carrier gas, a high p-xylene approach to equilibrium could be maintained for several days.

The zeolite TPZ-3 catalyst also has the advantage that when its activity is reduced after long-term use and the p-xylene approach to equilibrium is decreased, they can be restored to the original levels by simply raising the reaction temperature.

In the practice of the isomerizing reaction, sidereactions such as disproportionation or transalkylation may occur depending upon the reaction conditions such as the temperature, pressure and WHSV. To inhibit such side-reactions, various metals may be ion-exchanged with the zeolite TPZ-3 catalyst or deposited on it, or the zeolite TPZ-3 catalyst may be treated with steam or with an amine. Or it is also possible to add some amount of an amine such as propylamine or butylamine to the feedstocks.

(4) Isomerization of ethylbenzene to xylene

The isomerization of ethylbenzene to xylene is a reaction involving hydrogenation and dehydrogenation of the benzene ring as schematically shown below.

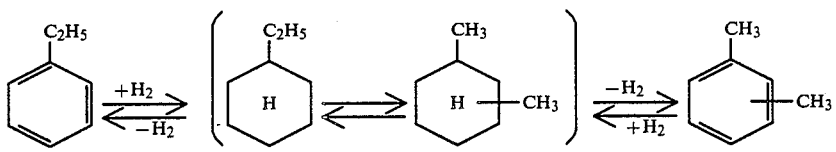

It is therefore necessary to use a zeolite TPZ-3 containing a catalyst with ion-exchanged and/or deposited metal having hydrogenating and dehydrogenating ability. Advantageously, the aforesaid zeolite TPZ-3 and a catalyst containing metals with hydrogenating and dehydrogenating activity deposited on an ordinary carrier are used in combination.

Examples of the metal having hydrogenating and dehydrogenating ability are iron, cobalt, nickel, copper, zinc, rhodium, ruthenium, iridium, palladium, rhenium, osmium and platinum. They may be used either singly or as a mixture of two or more. When two or more of them are used in combination, it is preferred to use a combination of platinum with at least one metal selected from the group consisting of iridium, palladium, rhodium, rhenium, osmium and lead.

The ethylbenzene to be submitted to the isomerization reaction needs not to be completely pure. It may be a mixture with the xylene isomers described in the isomerization reaction of xylenes above. $C_8$-Aromatic hydrocarbon fractions obtained by reforming, thermal cracking or hydrocracking of naphtha can be used especially advantageously. These fractions contain ethylbenzene of the same number of carbons in addition to the xylene isomers. Such $C_8$-aromatic hydrocarbon fractions usually contain the xylene isomers and ethylbenzene in a total amount of at least 80%, preferably at least 90% by weight, based on the weight of the fractions.

This isomerization reaction can be carried out at the same temperature, pressure and WHSV as described above with regard to the isomerization of xylenes, provided that the presence of hydrogen in the feedstock is essential in this isomerization reaction. The amount of hydrogen is generally 1 to 20 moles, preferably 1 to 20 moles, per mole of the entire hydrocarbons in the feedstock.

According to the isomerization reaction of ethylbenzene to xylenes in the presence of the zeolite TPZ-3 of the invention as a catalyst, the catalyst has high xylene isomerizing activity and undergoes little degradation. Hence, the reaction can be carried out at relatively low temperatures and pressures, and the loss of xylenes owing to the undesired side-reactions, i.e. disproportionation and transalkylation of ethylbenzene and xylenes.

Accordingly, the selectivity of xylenes from ethylbenzene can be maintained at a high level.

The following Examples illustrate the present invention more specifically.

PART I: ZEOLITE

I-(1): SYNTHESIS OF ZEOLITE

EXAMPLE 1

Methyl iodide (50 g) was added to 800 ml of an ethanol solution of 25 g of N,N,N',N'-tetramethyl-1,6-hexanediamine. Mild heat generation lasted for about 3 hours, and a precipitate formed. While the light was shut off, the mixture was stirred further for one day. The resulting white powder was separated by filtration, washed with acetone and dried under reduced pressure to give N,N,N,N',N',N'-hexamethyl-1,6-hexane diammonium salt almost quantitatively.

77 g of water glass (a product of Wako Pure Chemicals Co., Ltd.; $SiO_2$ 30.88 wt.%, $Na_2O$ 16.86 wt.%, $H_2O$ 44.56 wt%) as a silica source, 3.32 g of aluminum sulfate 18-hydrate (special reagent grade; a product of Wako Pure Chemicals Co. Ltd.) as an alumina source, 13.50 g of sulfuric acid (98%; special reagent grade, a product of Wako Pure Chemicals Co., Ltd.) as a neutralizing agent and 4.56 g of N,N,N,N',N',N'-hexamethyl-1,6-hexanediammonium salt prepared as above as an organic ammonium compound were added to 200 ml of deionized water to form a gel having the following composition in terms of mole ratios.

$SiO_2/Al_2O_3 = 100$
Ammonium salt/Si+Al = 0.02
$OH^-/Si+Al = 0.20$
$H_2O/Si+Al = 25.7$
$OH^-/H_2O = 7.8 \times 10^{-3}$ The gel was fed into a 500 ml stainless steel autoclave, and with gentle stirring, reacted at 160° C. under autogenous pressure for one week.

The reaction mixture was withdrawn, and filtered. The filtrate was washed with deionized water fully until the washing had an electric conductivity of less than 50 $\mu$/cm. The product was dried at 60° C. overnight to give 24.2 g of crystalline zeolite TPZ-3.

This zeolite TPZ-3 had the following composition in terms of the mole ratios of oxides.

0.63 RO; 0.88 $Na_2O$; $Al_2O_3$; 62.7 $SiO_2$; 11.2 $H_2O$ (R = N,N,N,N',N',N'-hexamethyl-1,6-hexane diammonium salt)

The X-ray diffraction data of this zeolite are shown in Table 1, and its X-ray diffraction pattern is shown in FIG. 1.

TABLE 1

| d (Å) | I/Io (%) |
|---|---|
| 20.1 | 81 |
| 11.19 | 49 |
| 9.94 | 41 |
| 6.92 | 2.7 |
| 5.83 | 4.0 |
| 5.64 | 4.0 |
| 4.98 | 5.3 |
| 4.67 | 39 |
| 4.33 | 100 |
| 4.02 | 56 |
| 3.83 | 28 |
| 3.72 | 17 |
| 3.65 | 4.0 |
| 3.44 | 32 |
| 3.33 | 41 |
| 3.28 | 35 |
| 3.21 | 13 |
| 3.15 | 5.3 |
| 3.10 | 4.0 |
| 2.96 | 6.7 |
| 2.84 | 1.3 |
| 2.71 | 4.0 |
| 2.54 | 6.7 |

This TPZ-3 zeolite will be referred to hereinbelow as Z-1.

When this zeolite was heated at 800° C. for 12 hours in the air, its X-ray diffraction remained substantially the same.

In the table, $I/I_o$ shows the ratio of the intensity of a ortwin peak to the intensity of the strongest peak (4.33 d(Å)) which is taken as 100. This applies to all of the following examples.

EXAMPLE 2

A gel was prepared in the same way as in Example 1 except that the amount of sulfuric acid was changed to 18.4 g, and the amount of the N,N,N,N',N',N'-hexamethyl-1,6-hexanediammonium salt was changed to 5.14 g. The resulting gel had the following composition in mole ratios.

$SiO_2/Al_2O_3 = 100$
Ammonium salt/Si+Al = 0.02
$OH^-/Si+Al = 0.008$
$H_2O/Si+Al = 25.2$
$OH^-/H_2O = 3 \times 10^{-4}$ The gel was reacted in the same way as in Example 1 to give 32.8 g of zeolite TPZ-3 having the following composition in terms of the mole ratios of oxides.

0.86 RO; 0.94 $Na_2O$; $Al_2O_3$; 75.2 $SiO_2$; 13.7 $H_2O$ (R is as indicated in Example 1)

Figure 2:
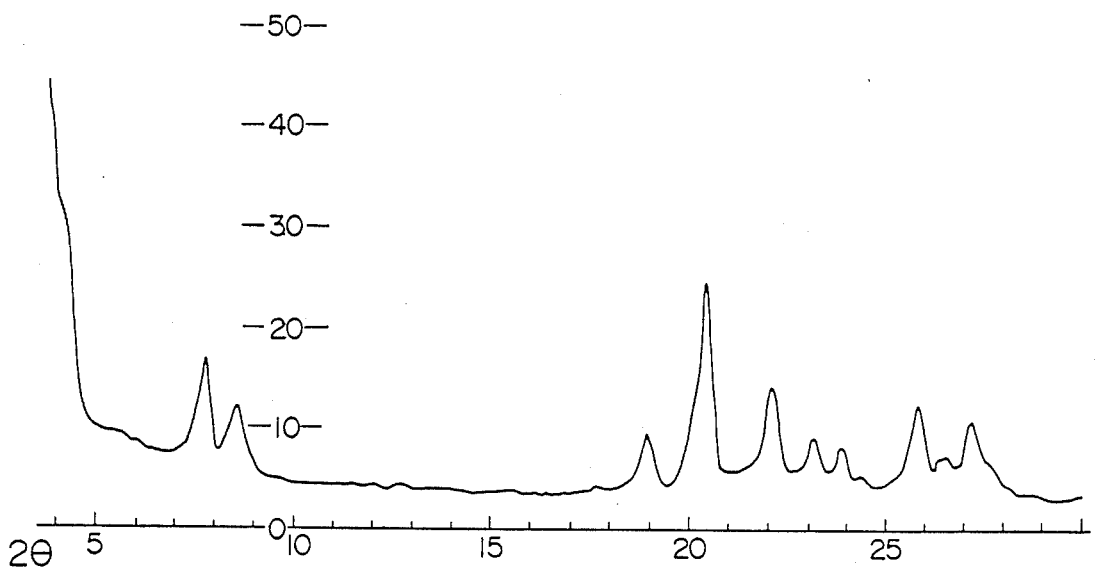

The X-ray diffraction data and chart of the product are shown in Table 2 and FIG. 2, respectively. From the absolute intensity, it is presumed that this TPZ-3 has a lower purity than Z-1 obtained in Example 1.

TABLE 2

| d (Å) | I/Io (%) |
|---|---|
| 11.33 | 56 |
| 10.28 | 36 |
| 5.01 | 2.6 |
| 4.70 | 28 |
| 4.33 | 100 |
| 4.02 | 51 |
| 3.83 | 21 |
| 3.72 | 15 |
| 3.66 | 2.6 |
| 3.45 | 46 |
| 3.36 | 21 |
| 3.28 | 7.5 |
| 3.21 | Sh |
| 3.10 | 5.1 |
| 2.96 | 7.7 |
| 2.74 | 5.1 |
| 2.54 | 5.1 |

(Sh shows a shoulder peak.)

The resulting TPZ-3 zeolite will be referred to hereinbelow as Z-2.

When this product was heat-treated at 800° C. in the same way as in Example 1, its X-ray diffraction data remained the same, and showed the good thermal stability of Z-2.

EXAMPLE 3

100 g of silica sol (CATALOID S-30L, $SiO_2$ 30 wt%; a tradename for a product of Catalytic Chemical Co., Ltd.) as a silica source, 1.27 g of sodium aluminate (a product of Wako Pure Chemical Co., Ltd.; $Na_2O:Al_2O_3=1.56:1$) as an alumina source, 4.16 g of sodium hydroxide (98%, special reagent grade, a product of Wako Pure Chemical Co., Ltd.) as an $OH^-$ source, 4.56 g of the N,N,N,N',N',N'-hexamethyl-1,6-hexane diammonium salt synthesized in Example 1 as an organic ammonium compound, and 30 g of sodium sulfate decahydrate (a special reagent grade; a product of Wako Pure Chemicals Co., Ltd.) were added to 150 ml of deionized water to prepare a gel.

The gel had the following composition.
$SiO_2/Al_2O_3=100$
Ammonium salt/Si+Al=0.02
$OH^-$/Si+Al=0.20
$H_2O$/Si+Al=24.0
$OH^-/H_2O=8.4\times10^{-3}$ The gel was reacted in the same way as in Example 1 to give 28.0 g of TPZ-3 zeolite. When calcined at 800° C. for 6 hours, this zeolite showed the following composition in terms of the mole ratios of oxides in the anhydrous state.

1.31 $Na_2O$; $Al_2O_3$; 76.9 $SiO_2$.

Figure 3:
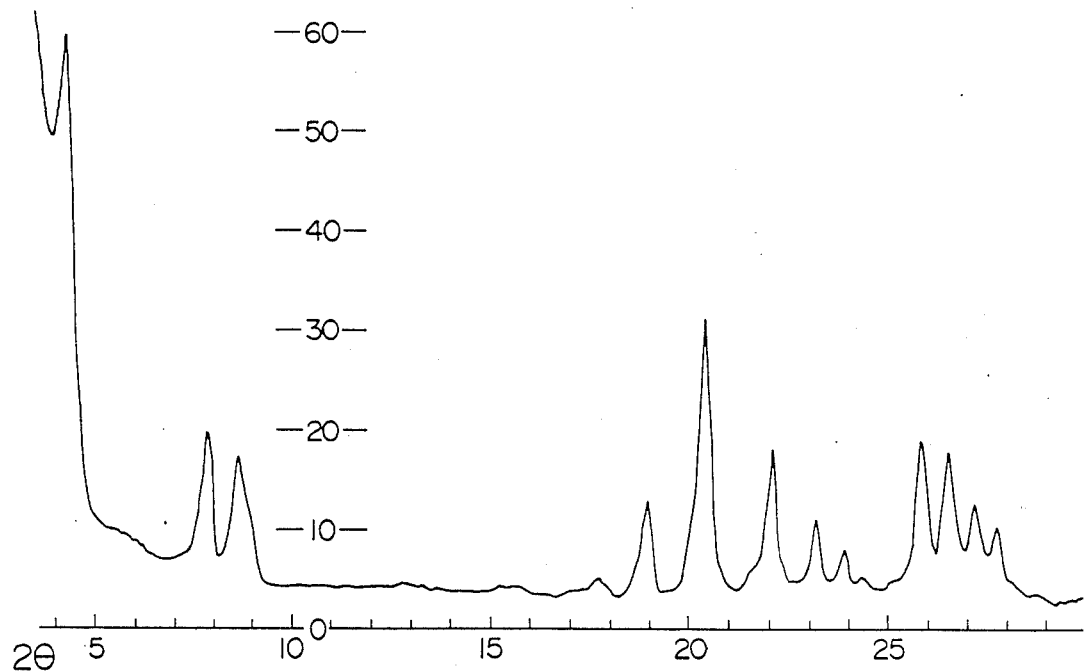

It showed the X-ray diffraction data and chart given in Table 3 and FIG. 3, respectively.

The TPZ-3 zeolite obtained will be referred to as Z-3.

TABLE 3

| d (Å) | I/Io (%) |
|---|---|
| 20.1 | 102 |
| 11.19 | 51 |
| 10.16 | 44 |
| 5.79 | 3.6 |
| 5.64 | 3.6 |
| 4.98 | 7.3 |
| 4.67 | 36 |
| 4.33 | 100 |
| 4.02 | 51 |
| 3.83 | 26 |
| 3.72 | 15 |
| 3.66 | 3.6 |
| 3.44 | 56 |
| 3.36 | 53 |
| 3.28 | 36 |
| 3.22 | 27 |
| 3.10 | 3.6 |
| 2.96 | 9.1 |
| 2.84 | 1.8 |
| 2.71 | 3.6 |
| 2.55 | 5.5 |

EXAMPLE 4

A gel was prepared from 250 g of silica sol as a silica source, 16.66 g of aluminum sulfate 18-hydrate is an alumina source, 13.89 g of sodium hydroxide as an $OH^-$ source, 60 g of N,N,N',N'-tetramethyl-1,6-hexanediamine, 9.9 g of methyl iodide and 500 g of deionized water.

The resulting gel had the following composition in mole ratios.
$SiO_2/Al_2O_3=50$
Ammonium salt/Si+Al=0.027
$OH^-$/Si+Al=0.10
$H_2O$/Si+Al=28.9
$OH^-/H_2O=3.5\times10^{-3}$ The gel was charged into a 1-liter stainless steel autoclave, and with gentle stirring, reacted at 160° C. under autogenous pressure for one week.

The reaction mixture was withdrawn, and filtered. The filtrate was washed with deionized water until the washing had an electric conductivity of less than 50 $\mu$/cm. The product was then dried at 60° C., to give 81.5 g of zeolite.

Figure 4:
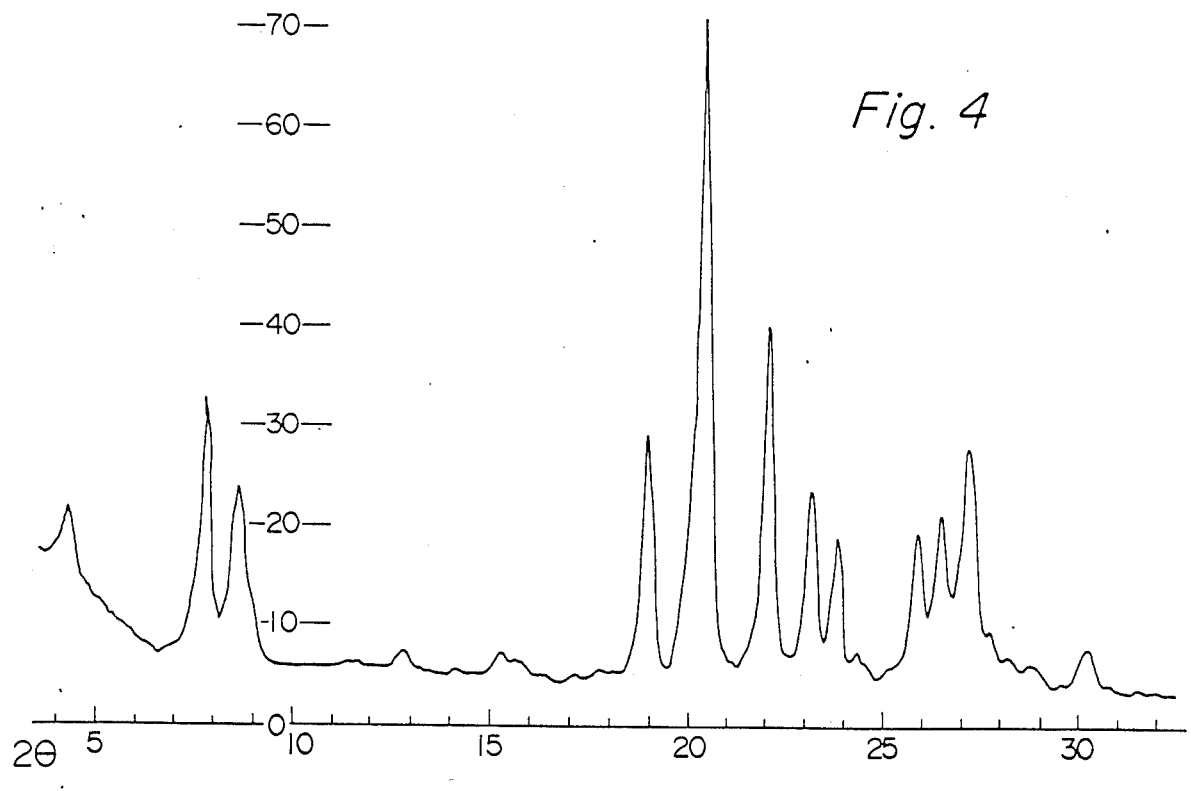

This zeolite had an X-ray diffraction pattern shown in FIG. 4 and Table 4 and was determined to be TPZ-3.

On analysis, this zeolite was found to contain 1.35% of H, 5.81% of C and 1.15% of N, and the ratio of N to C was 0.170 (theoretical value 0.194).

The resulting TPZ-3 zeolite will be referred to hereinbelow as Z-4.

TABLE 4

| d (Å) | I/Io (%) |
|---|---|
| 20.32 | 8.4 |
| 11.19 | 39.3 |
| 10.22 | 26.3 |
| 9.83 | Sh |
| 6.916 | 3.3 |
| 5.848 | 3.8 |
| 5.644 | 2.7 |
| 4.983 | 2.3 |
| 4.631 | 37.5 |
| 4.332 | 100 |
| 4.022 | 54.1 |
| 3.834 | 29.3 |
| 3.731 | 22.5 |
| 3.655 | 4.8 |
| 3.440 | 23.1 |
| 3.363 | 25.5 |
| 3.278 | 36.0 |
| 3.209 | 8.3 |
| 3.164 | 4.8 |
| 3.100 | 3.9 |
| 2.959 | 6.3 |
| 2.714 | 3.5 |
| 2.543 | 6.0 |
| 2.491 | 1.8 |
| 2.417 | 3.8 |
| 2.327 | 3.0 |
| 2.304 | 2.7 |

EXAMPLE 5

3315 g of water glass (a product of Wako Pure Chemicals Co., Ltd.; $SiO_2$ 36.24 wt. %, $Na_2O$ 17.30 wt. %; $H_2O$ 46.46 wt. %) as a silica source, 266 g of aluminum sulfate 18-hydrate as an alumina source, 668 g of sulfuric acid as a neutralizing agent 500 g of sodium chloride, 339 g of N,N,N',N'-tetramethyl-1,6-hexanediamine and 567 g of methyl iodide were added to 10 liters of deionized water to prepare a gel.

The gel had the following composition in mole ratios.
$SiO_2/Al_2O_3=50$
Ammonium salt/Si+Al=0.096 $OH^-$/Si+Al=0.10
$H_2O$/Si+Al=30.9
$OH^-/H_2O=3.3\times10^{-3}$ The gel was charged into 20-liter stainless steel autoclave, and with gentle stirring, reacted at 160° C. under autogenous pressure for one week.

Figure 5:
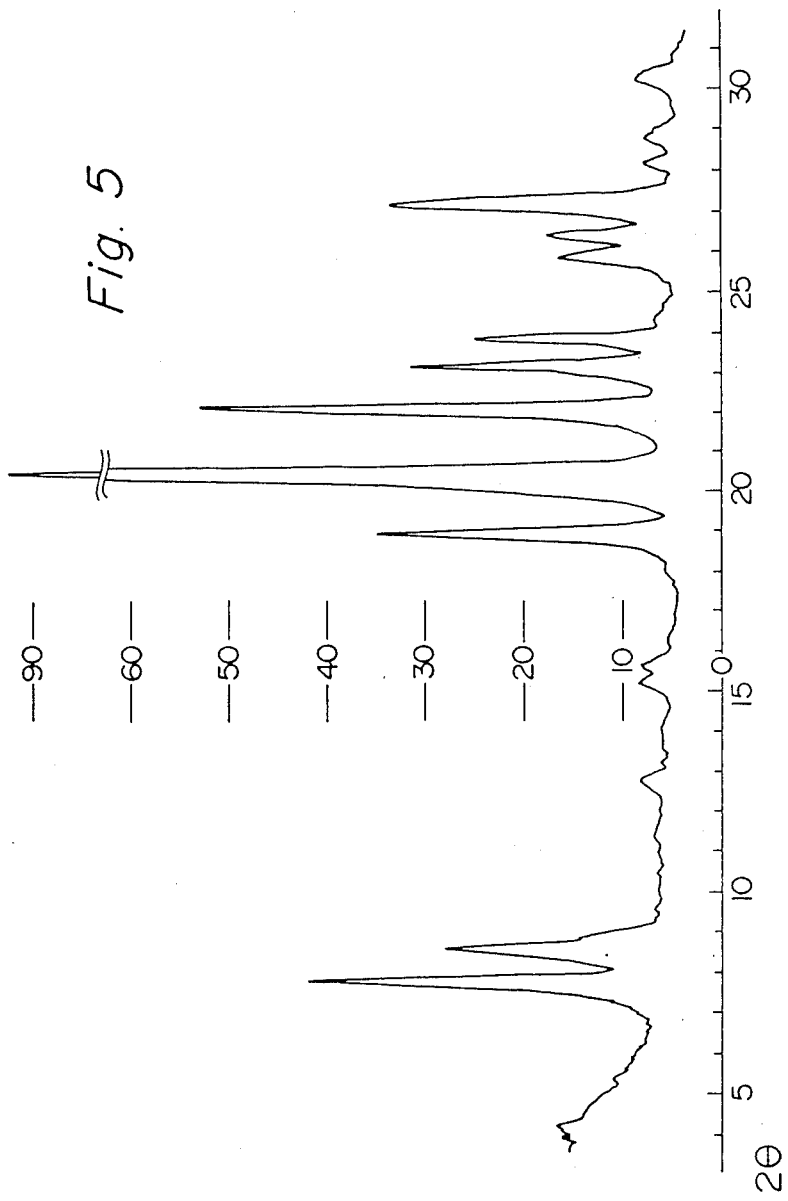

The reaction mixture was withdrawn and filtered. The filtrate was washed with deionized water until the washing had an electric conductivity of less than 50 $\mu$/cm. The product was dried overnight at 60° C. The product weighed 1.2 kg, and from the X-ray diffraction pattern and data shown in FIG. 5 and Table 5, respectively, was determined to be TPZ-3 zeolite.

The zeolite obtained had the following composition in terms of the mole ratios of oxides.

1.26 RO; 0.21 $Na_2O$; $Al_2O_3$; 42.03 $SiO_2$; 4.75 $H_2O$. The ratio of N to C was 0.167.

The resulting zeolite will be referred to as Z-5 hereinafter.

TABLE 5

| d (Å) | I/Io |
| --- | --- |
| 21.04 | 1.7 |
| 11.26 | 40.3 |
| 10.28 | 24.4 |
| 9.94 | 8.5 |
| 6.916 | 2.8 |
| 5.829 | 4.0 |
| 5.662 | 3.6 |
| 4.683 | 34.7 |
| 4.343 | 100 |
| 4.022 | 54.5 |
| 3.834 | 30.1 |
| 3.723 | 22.7 |
| 3.440 | 12.5 |
| 3.376 | 14.2 |
| 3.284 | 33.0 |
| 3.164 | 3.4 |
| 3.100 | 3.4 |
| 2.840 | 5.1 |
| 2.714 | 3.4 |
| 2.553 | 6.8 |
| 2.481 | 1.7 |
| 2.417 | 4.3 |
| 2.327 | 2.8 |
| 2.304 | 2.8 |

EXAMPLE 6

A gel was prepared from 4144 g of water glass (a product of Wako Pure Chemicals Co., Ltd.; $SiO_2$ 36.24 wt. %, $Na_2O$ 17.30 wt. %, $H_2O$ 46.46 wt. %) as a silica source, 167 g of aluminum sulfate 18-hydrate as an alumina source, 809 g of sulfuric acid as a neutralizing agent, 500 g of sodium chloride, 341 g of N,N,N',N'-tetramethyl-1,6-hexanediamine, 571 g of methyl iodide and 10 liters of deionized water.

Figure 6:
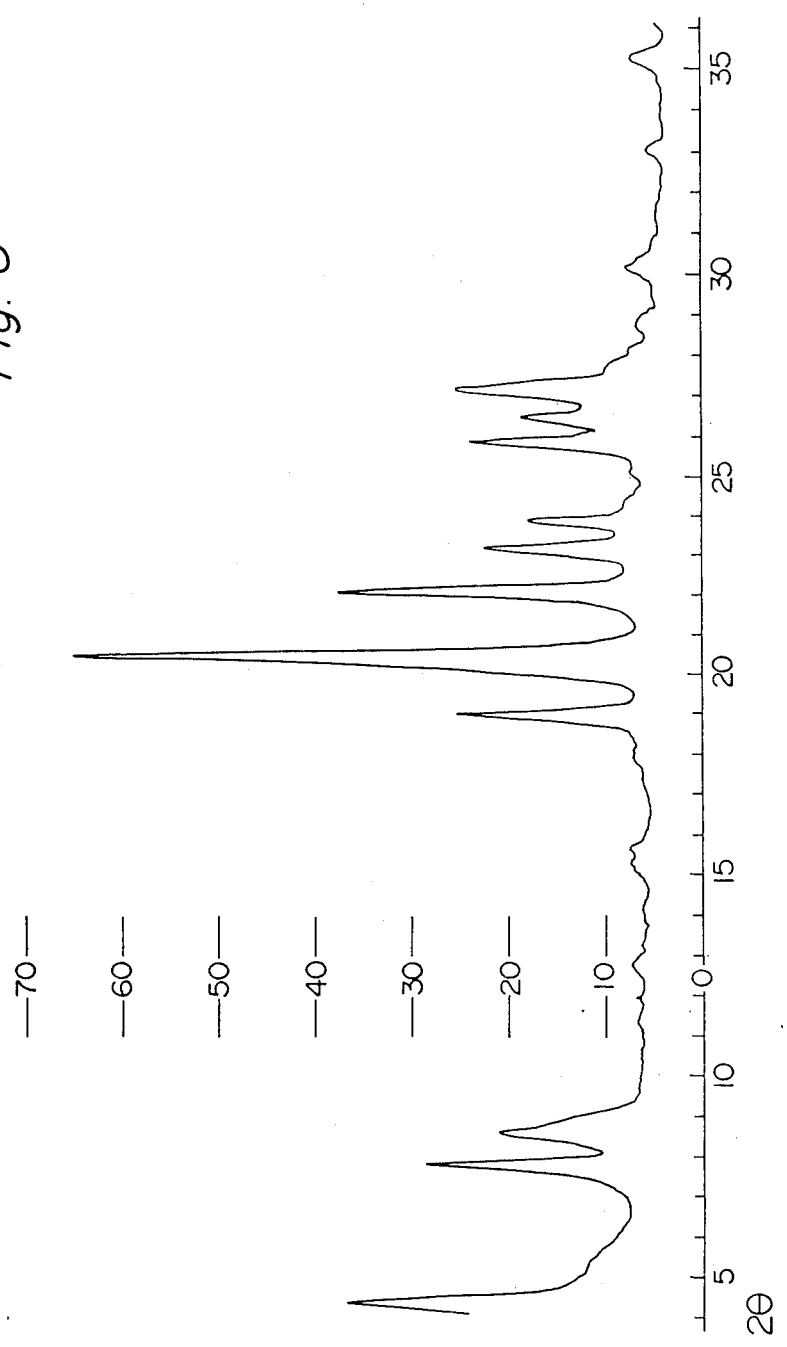

The gel had the following composition in mole ratios.
$SiO_2/Al_2O_3 = 99.6$
Ammonium salt/Si+Al = 0.079
$OH^-/Si+Al = 0.200$
$H_2O/Si+Al = 26.3$
$OH^-/H_2O = 7.6 \times 10^{-3}$ The gel was charged into a 20-liter stainless steel autoclave, and with gentle stirring, reacted at 160° C. under autogenous pressure for one week. The reaction mixture was withdrawn and filtered. The filtrate was washed with deionized water until the washing had an electric conductivity of less than 50 μ /cm. The product was dried overnight at 60° C. The product weighed 1.3 kg, and from the X-ray diffraction pattern and the X-ray diffraction data shown in FIG. 6 and Table 6 respectively, was determined to be TPZ-3.

The zeolite TPZ-3 obtained had the following composition in terms of the mole ratios of oxides.

1.55 RO; 0.89 $Na_2O$; $Al_2O_3$; 64.00 $SiO_2$; 10.70 $H_2O$

The ratio between N and C detected was 0.171.

The resulting TPZ-3 zeolite will be referred to hereinafter as Z-6.

TABLE 6

| d (Å) | I/Io |
| --- | --- |
| 20.08 | 36.0 |
| 11.31 | 36.0 |
| 10.28 | 23.8 |
| 10.05 | Sh |
| 9.83 | Sh |
| 6.916 | 2.2 |
| 5.791 | 2.8 |
| 5.662 | 3.0 |
| 4.928 | 3.0 |
| 4.678 | 33.8 |
| 4.336 | 100 |
| 4.022 | 53.3 |
| 3.839 | 28.8 |
| 3.723 | 21.2 |
| 3.663 | 5.0 |
| 3.534 | 4.2 |
| 3.440 | 31.6 |
| 3.363 | 22.7 |
| 3.284 | 33.8 |
| 3.209 | 8.7 |
| 3.164 | 4.7 |
| 3.100 | 3.5 |
| 2.959 | 5.3 |
| 2.710 | 3.2 |
| 2.550 | 5.8 |
| 2.481 | 1.7 |
| 2.414 | 3.8 |
| 2.327 | 2.3 |
| 2.301 | 2.3 |

EXAMPLE 7

A gel was prepared from 4 kg of silica sol as a silica source, 266 g of aluminum sulfate 18-hydrate as an alumina source, 222 g of sodium hydroxide as a neutralizing agent, 358 g of N,N,N',N'-tetramethyl-1,6-hexanediamine as an organic ammonium ion source, 590 g of methyl iodide and 8.5 liters of deionized water. The gel had the following composition in mole ratios.

Figure 7:
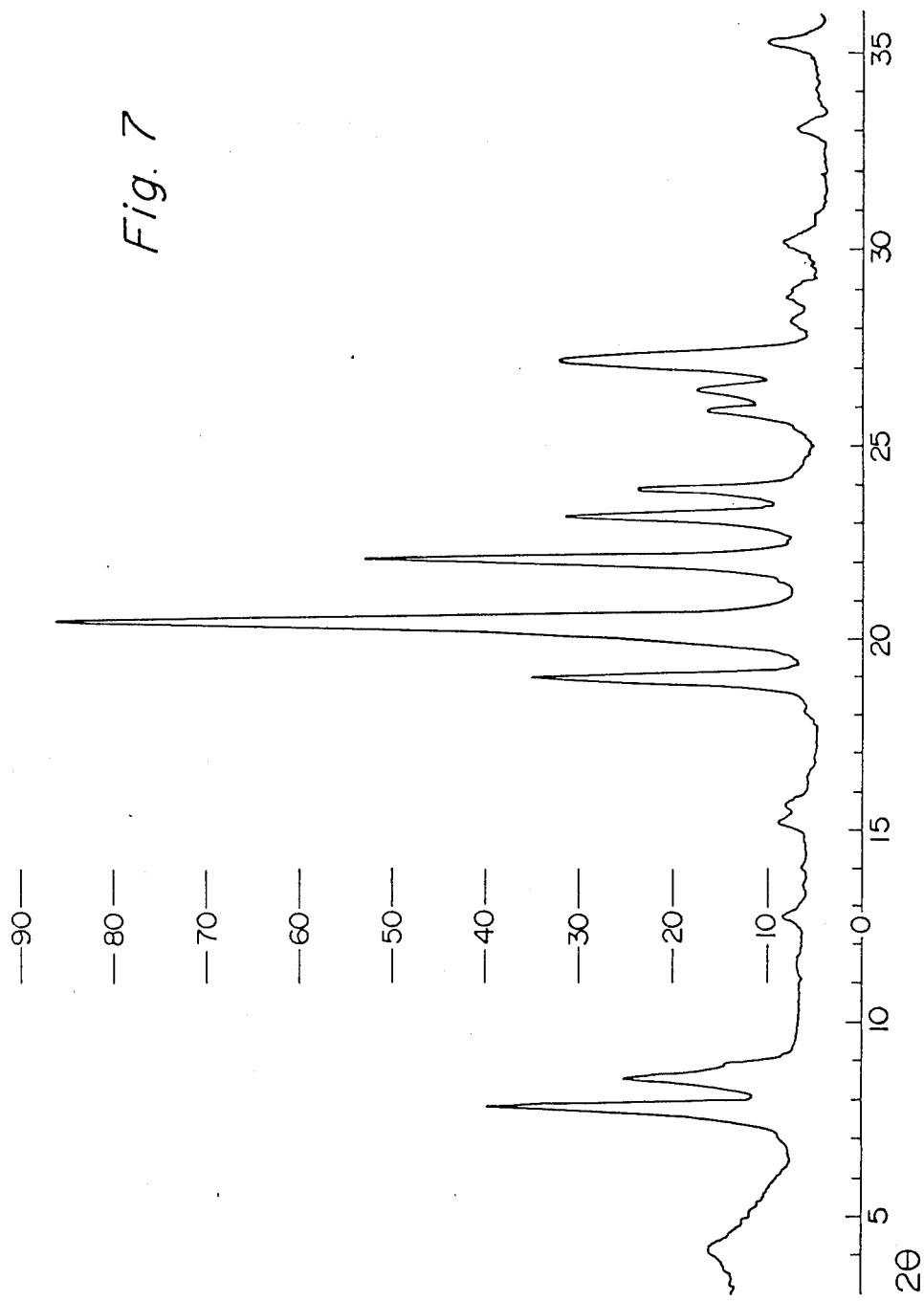

$SiO_2/Al_2O_3 = 50.1$
Ammonium salt/Si+Al = 0.100
$OH^-/Si+Al = 0.100$
$H_2O/Si+Al = 30.2$
$OH^-/Si+Al = 3.3 \times 10^{-3}$ The gel was charged into a 20-liter autoclave, and with gentle stirring, reacted at 160° C. under autogenous pressure for one week. The reaction mixture was withdrawn and filtered. The filtrate was washed with deionized water until the washing had an electric conductivity of less than 50 μ /cm. The product was dried overnight at 60° C. The product weighed 1.4 kg, and from the X-ray diffraction pattern and the X-ray diffraction data shown in FIG. 7 and Table 7, was determined to be zeolite TPZ-3.

The zeolite had the following composition in terms of the mole ratios of oxides.

1.23 RO; 0.17 $Na_2O$; $Al_2O_3$; 40.56 $SiO_2$; 6.82 $H_2O$.

The ratio between C and N detected was 0.159.

The resulting TPZ-3 zeolite will be referred to hereinbelow as Z-7.

TABLE 7

| d (Å) | I/Io |
| --- | --- |
| 11.29 | 42.1 |
| 10.28 | 23.5 |
| 9.94 | 9.4 |
| 6.943 | 3.1 |
| 5.829 | 4.4 |
| 5.644 | 4.0 |
| 4.901 | 1.9 |
| 4.671 | 37.5 |
| 4.339 | 100 |
| 4.022 | 60.0 |
| 3.834 | 32.9 |
| 3.723 | 23.5 |
| 3.440 | 14.4 |
| 3.376 | 15.4 |
| 3.278 | 34.0 |
| 3.164 | 3.9 |
| 3.100 | 4.4 |
| 2.959 | 5.6 |
| 2.710 | 3.9 |
| 2.546 | 7.9 |
| 2.481 | 2.5 |

TABLE 7-continued

| d (Å) | I/Io |
|---|---|
| 2.414 | 4.6 |
| 2.327 | 2.9 |
| 2.301 | 2.9 |

EXAMPLES 8 TO 16

Using silica sol as a silica source, aluminum sulfate 18-hydrate as an alumina source, sodium hydroxide as an $OH^-$ source, and N,N,N,N',N',N'-hexamethyl-1,6-hexanediammonium salt synthesized in Example 1 as an ammonium ion source, zeolites were prepared under the conditions shown in Table 8.

The results are shown in Table 8 together with those obtained in Examples 1 to 7.

EXAMPLES 17 TO 26

Using water glass as a silica source, aluminum sulfate 18-hydrate as an alumina source, sulfuric acid as a neutralizing agent, the N,N,N,N',N',N'-hexamethyl-1,6-hexanediammonium salt synthesized in Example 1 as an ammonium source, a tetramethyl ammonium salt, a tetraethyl ammonium salt and TPZ-3 obtained in Example 4 as a seed, zeolites were synthesized under the conditions shown in Table 9.

In Table 9, the following abbreviations are used.
R: N,N,N,N',N',N'-hexamethyl-1,6-hexane diammonium salt
DBSNa: sodium dodecylbenzenesulfonate
Et$_4$NBr: tetraethyl ammonium bromide
Et$_4$NCl: tetraethyl ammonium chloride
Me$_4$NCl: tetramethyl ammonium chloride

TABLE 8

| Zeolite | Example | Composition of the reaction mixture | | | | Reaction conditions | | Product |
|---|---|---|---|---|---|---|---|---|
| | | SO$_2$/Al$_2$O$_3$ mole ratio | OH$^-$/Si + Al mole ratio | OH$^-$/H$_2$O mole ratio | Ammonium salt/Si + Al mole ratio | Temperature (°C.) | Time (days) | |
| Z-1 | 1 | 100 | 0.20 | 7.8 × 10$^{-3}$ | 0.02 | 160 | 7 | TPZ-3 |
| Z-2 | 2 | " | 0.008 | 0.3 × 10$^{-3}$ | " | " | " | " |
| Z-3 | 3 | " | 0.20 | 8.4 × 10$^{-3}$ | " | " | " | " |
| Z-4 | 4 | 50 | 0.10 | 3.5 × 10$^{-3}$ | 0.027 | " | " | " |
| Z-5 | 5 | " | " | 3.3 × 10$^{-3}$ | 0.096 | " | " | " |
| Z-6 | 6 | 99.6 | 0.20 | 7.6 × 10$^{-3}$ | 0.079 | " | " | " |
| Z-7 | 7 | 50.1 | 0.10 | 3.3 × 10$^{-3}$ | 0.100 | " | " | " |
| Z-8 | 8 | 5 | 0.50 | 13.4 × 10$^{-3}$ | 0.01 | " | 6 | Analcime |
| Z-9 | 9 | " | 0.20 | 9.1 × 10$^{-3}$ | " | " | 7 | Analcime + Mordenite |
| Z-10 | 10 | 100 | 0.10 | 4.2 × 10$^{-3}$ | 0.02 | 170 | 6 | TPZ-3 (+ the peak whose assignment is not known) |
| Z-11 | 11 | 80 | " | " | " | 160 | " | TPZ-3 (+ the peak whose assignment is not known) |
| Z-12 | 12 | 100 | 0.20 | 8.3 × 10$^{-3}$ | 0 | " | 8 | α-Quartz + Mordenite |
| Z-13 | 13 | 100 | 0.20 | 8.3 × 10$^{-3}$ | 0.02 | 200 | 8 | TPZ-3 + α-Quartz |
| Z-14 | 14 | 200 | 0.20 | " | " | 170 | 7 | " |
| Z-15 | 15 | 80 | 0.10 | 4.2 × 10$^{-3}$ | " | 200 | " | " |
| Z-16 | 16 | 100 | 0.20 | 8.4 × 10$^{-3}$ | " | 160 | 6 | TPZ-3 + trace Mordenite |

(*): the asterisk means that silica sol, sodium aluminate and sodium hydroxide were used.

TABLE 9

| Example | Zeolite | Compositon of the reaction of the mixture | | | | Additive | | Reaction conditions | Product |
|---|---|---|---|---|---|---|---|---|---|
| | | SiO$_2$/Al$_2$O$_3$ | OH$^-$/Si + Al | OH$^-$–H$_2$O | Ammonium salt/Si + Al | | | | |
| 17 | Z-17 | 50 | 0.10 | 4.7 × 10$^{-3}$ | 0.21 | R + Et$_4$NCl | 4NCl/R = 3.4 (mole) | 160°, 7 days. | TPZ-3 |
| 18 | Z-18 | 50 | 0.20 | 6.3 × 10$^{-3}$ | 0.21 | R + Et$_4$NBv | Et$_4$NBr/R = 3.4 (mole) | 160°, 5 days, 130°, 1 day, 100°, 1 day. | TPZ-3 |
| 19 | Z-19 | 50 | 0.20 | 6.3 × 10$^{-3}$ | 0.21 | R + Et$_4$NBr | Et$_4$NBr/R = 3.4 (mole) | 100°, 1 day, 130°, 1 day, 160°, 5 days, | TPZ-3 |
| 20 | Z-20 | 50 | 0.20 | 6.3 × 10$^{-3}$ | 0.21 | R + Et$_4$NBr | Et$_4$NBr/R = 3.4 (mole) | 100°, 1 day, 130°, 1 day, 160°, 3 days, 130°, 1 day, 100°, 1 day. | TPZ-3 |
| 21 | Z-21 | 50 | 0.20 | 6.3 × 10$^{-3}$ | 0.21 | R + Et$_4$NBr + DBSNa | Et$_4$NBr/R = 3.4 (mole) DBSNa/Si + Al = 4.6 × 10$^{-3}$ (mole) | 160°, 5 days, 130°, 1 day 100°, 1 day. | TPZ-3 |
| 22 | Z-22 | 60 | 0.26 | 13.9 × 10$^{-3}$ | 0.06 | Et$_4$NCl | | 160°, 4 days. | Trace Mordenite |
| 23 | Z-23 | 50 | 0.20 | 6.3 × 10$^{-3}$ | 0.21 | R + Me$_4$NCl | Me$_4$NCl/R = 3.4 (mole) | 160°, 5 days, 130°, 1 day, | TPZ-3 |

TABLE 9-continued

| Example | Zeolite | SiO$_2$/Al$_2$O$_3$ | OH$^-$/Si + Al | OH$^-$H$_2$O | Ammonium salt/Si + Al | Additive | | Reaction conditions | Product |
|---|---|---|---|---|---|---|---|---|---|
| | | | | | | | | 100°, 1 day. | |
| 24 | Z-24 | 50 | 0.50 | 11.6 × 10$^{-3}$ | 0.08 | Me$_4$NCl | | 160°, 6 days. | Fu-1(*) |
| 25 | Z-25 | 50 | 0.10 | 4.0 × 10$^{-3}$ | 0.04 | R + seed | seed/ SiO$^4$ + Al$_2$O$_3$ = 0.05 (wt.) | 160°, 8 days. | TPZ-3 |
| 26 | Z-26 | 50 | 0.20 | 6.3 × 10$^{-3}$ | 0.05 | R + seed | seed/ SiO$_2$ + Al$_2$O$_3$ = 0.06 (wt.) | 160°, 5 days, 130°, 1 day, | TPZ-3 |

(*) Fu-1: The synthetic zeolite shown in U.S. Pat. No. 4,209,498.

I-(2): MODIFICATION OF ZEOLITES

EXAMPLE 27 (synthesis of H-form zeolite)

Fifteen grams of TPZ-3 (Z-5) was calcined at 500° C. for 6 hours, and converted into ammonium form by ion-exchange with 100 ml of a 10% ammonium chloride aqueous solution under reflux. This ion-exchanging was repeated three times. The product was filtered, washed and again dried. It was calcined in an electric muffle furnace at 500° C. for 6 hours to form an H-form TPZ-3. The product will be referred to as HZ-5.

Similarly, various TPZ-3 zeolites were subjected to ion-exchange. After the ion exchange, the zeolites had a very low sodium content as shown in Table 10. This shows that the zeolites were almost completely ion-exchanged.

The H$^+$-TPZ-3 zeolites had substantially the same X-ray diffraction patterns as those before ion exchange. These X-ray diffraction patterns remained unchanged even when they were heat-treated at 800° C.

15 g of the resulting HZ-5 was ion-exchanged under reflux by using 100 ml of a 10% aqueous solution of sodium chloride. This ion-exchanging was repeated three times. The product was filtered and washed and again dried. The product was calcined in an electric muffle furnace at 500° C. for 6 hours to give NaZ-5-1. Similarly, NaZ-6 and NaZ-7 were obtained from HZ-6 and HZ-7. The sodium contents of these products are shown in Table 11.

As a comparative example, the results obtained with ZSM-5 synthesized in accordance with the specification of U.S. Pat. No. 3,965,207 are also shown in Tables 10 and 11.

TABLE 10

| Type of H$^+$—TPZ-3 | Na$_2$O/Al$_2$O$_3$ (mole ratio) |
|---|---|
| HZ-1 | 0.04 |
| HZ-2 | 0.02 |
| HZ-3 | 0.06 |
| HZ-5 | 0.02 |
| HZ-6 | 0.04 |
| HZ-7 | 0.01 |
| HZ-10 | 0.02 |
| HZ-11 | 0.01 |
| HZ-16 | 0.04 |
| Comparison H-ZSM-5 | 0.02 |

TABLE 11

| Type of Na$^+$—TPZ-3 | Na$_2$O/Al$_2$O$_3$ (mole ratio) |
|---|---|
| NaZ-5-1 | 0.74 |
| NaZ-6 | 1.01 |
| NaZ-7 | 0.68 |
| Comparison Na—ZSM-5 | 0.88 |

5.0 g of HZ-5 was contacted with an aqueous solution of sodium chloride at 70° C. to prepare TPZ-3 zeolites having introduced thereinto various amounts of alkali. The method of ion-exchange and the degree of exchange are shown in Table 12.

TABLE 12

| Zeolite | NaCl aq. sol. | Time of treatment (hrs) | Number of repetition | Na$_2$O/Al$_2$O$_3$ mole ratio |
|---|---|---|---|---|
| NaZ-5-2 | 67 mg/50 ml H$_2$O | 8 | 1 | 0.12 |
| NaZ-5-3 | 1.17 g/100 ml H$_2$O | 8 | 1 | 0.35 |
| NaZ-5-4 | 1.17 g/100 ml H$_2$O | 8 | 3 | 0.55 |

EXAMPLE 28 (measurement of the absorbing properties of zeolite)

The various powdery H-TPZ-3 and Na-TPZ-3 zeolites obtained in Example 27 were each calcined in an electric muffle furnace in an atmosphere of air at 450° C. for 8 hours in order to remove the adhering water. About 1 g of each of these zeolites was weighed into a weighing bottle. Then, the weighed zeolite was allowed to stand in a desiccator containing a solvent to be adsorbed, at 25° C. and 120±20 mmHg for 6 hours to permit the solvent to be adsorbed to the zeolite to saturation. Then, the solvent in the desiccator was removed, and the inside of the desiccator was evacuated for 2 hours at 25° C. and 120±20 mmHg. The amount of the solvent adsorbed to zeolite was calculated from the following equation.

$$v = \frac{W_2 - W_1}{W_1} \times 100\ (\%)$$

wherein v (%) is defined as the amount of adsorption per unit weight of zeolite, and W$_1$ and W$_2$ are the weights of zeolite before and after the adsorption, respectively.

The amounts of adsorptions obtained with regard to water, ethylbenzene (EB), p-xylene (PX), o-xylene (OX), n-hexane and cyclohexane and the cyclohexane/n-hexane sorption ratios (v cyclohexane/v n-hexane) are shown in Table 13 together with the results obtained with comparative zeolites.

TABLE 13

| Zeolite | $V_{H_2O}$ (%) | $V_{EB}$ (%) | $V_{PX}$ (%) | $V_{OX}$ (%) | $V_{n-hexane}$ (%) | $V_{cyclohexane}$ (%) | Cyclohexane/n-hexane sorption ratio |
|---|---|---|---|---|---|---|---|
| H+—TPZ-3 | | | | | | | |
| HZ-1 | 6.69 | | 3.88 | | 3.16 | 1.61 | 0.51 |
| HZ-2 | 5.35 | | 3.88 | | 1.64 | 1.20 | 0.73 |
| HZ-3 | 4.76 | | 4.46 | | 2.65 | 1.22 | 0.46 |
| HZ-5 | 9.47 | 4.28 | 10.41 | 4.58 | 7.35 | 6.10 | 0.83 |
| HZ-6 | 7.13 | 6.03 | 8.04 | 5.53 | 7.06 | 6.45 | 0.91 |
| HZ-7 | 8.81 | 9.33 | 10.69 | 5.95 | 9.15 | 7.93 | 0.87 |
| HZ-11 | 4.95 | | 5.03 | | 2.95 | 2.16 | 0.73 |
| H+—ZSM-5 (Comparison) | 8.12 | 9.25 | 7.95 | 7.36 | 11.45 | 8.44 | 0.74 |
| Zeolon 100H (Commercial product) | 14.80 | 5.92 | 6.09 | 9.17 | 7.26 | 8.97 | 1.24 |
| Zeolon 900H (Commercial product) | | | | | 9.07 | 9.21 | 1.02 |
| Na+—TPZ-3 | | | | | | | |
| NaZ-5-1 | | | | | 10.20 | 3.54 | 0.35 |
| NaZ-6 | | | | | 8.62 | 3.37 | 0.39 |
| NaZ-7 | | | | | 9.26 | 4.45 | 0.48 |
| Na+—ZSM-5 (Comparison) | 13.04 | 6.96 | 0.53 | | | | |
| Zeolon 900 Na (Commercial product) | | | | | 2.19 | 2.94 | 1.34 |

EXAMPLE 29

Various H+-TPZ-3 zeolites were each pelletized to a size of 10 to 20 mesh to obtain catalysts A-1 to A-7.

TABLE 14

| Catalyst | TPZ-3 |
|---|---|
| A-1 | HZ-1 |
| A-2 | HZ-2 |
| A-3 | HZ-3 |
| A-4 | HZ-4 |
| A-5 | HZ-5 |
| A-6 | HZ-6 |
| A-7 | HZ-7 |

(B) Each of various H+-TPZ-3 zeolites was fully mixed with an equal weight of chromatographic alumina gel, and the mixture was pelletized to a size of 10 to 20 mesh. Thus, catalysts B-1 to B-8 were prepared.

5 g of HZ-5 was contacted three times with 100 ml of a 5% strontium nitrate aqueous solution at 70° C. for 6 hours to perform ion-exchange. The TPZ-3 subjected to ion-exchange was collected by filtration, and washed until the washing had an ion conductivity of less than 50 μ /cm. The product was dried in an electric desiccator at 100° C. for 4 hours, and calcined in an electric muffle furnace at 500° C. for 8 hours. The calcined zeolite was mixed with an equal amount of chromatographic alumina gel, and the mixture was pelletized to a size of 10 to 20 mesh to give a catalyst B-14. In the same way as above except that the type of the inorganic salt was changed, catalysts B-9 to B-21 were each prepared.

In the above, the catalysts B-2, B-3, B-4, B-5, B-6, B-7 and B-8 were prepared by using HZ-17, HZ-18, HZ-19, HZ-20, HZ-21, HZ-23 and HZ-26 as starting materials. These starting materials were obtained respectively by converting Z-17, Z-18, Z-19, Z-20, Z-21, Z-23 and Z-26 into an H form.

TABLE 15

| Catalyst | $M^{n+}$—H+—TPZ-3 | TPZ-3 | Inorganic salt |
|---|---|---|---|
| B-1 | H+—TPZ-3 | HZ-5 | — |
| B-2 | H+—TPZ-3 | HZ-17 | — |
| B-3 | " | HZ-18 | — |
| B-4 | " | HZ-19 | — |
| B-5 | " | HZ-20 | — |
| B-6 | " | HZ-21 | — |
| B-7 | " | HZ-23 | — |
| B-8 | " | HZ-26 | — |
| B-9 | Li+—H+—TPZ-3 | HZ-5 | LiNO$_3$ |
| B-10 | K+—TPZ-3 | " | KCl |
| B-11 | Be++—TPZ-3 | " | Be(NO$_3$)$_2$.3H$_2$O |
| B-12 | Mg++—TPZ-3 | " | Mg(NO$_3$)$_2$.6H$_2$O |
| B-13 | Ca++—TPZ-3 | " | Ca(NO$_3$)$_2$.4H$_2$O |
| B-14 | Sr++—TPZ-3 | " | Sr(NO$_3$)$_2$ |
| B-15 | Ba++—TPZ-3 | " | Ba(NO$_3$)$_2$ |
| B-16 | La+++—TPZ-3 | " | La(NO$_3$)$_3$.6H$_2$O |
| B-17 | Ce+++—TPZ-3 | " | Ce(NO$_3$)$_3$.6H$_2$O |
| B-18 | Co++—TPZ-3 | " | Co(NO$_3$)$_2$.6H$_2$O |
| B-19 | Ni++—TPZ-3 | " | Ni(NO$_3$)$_2$.6H$_2$O |
| B-20 | Cu++—TPZ-3 | " | Cu(NO$_3$)$_2$.6H$_2$O |
| B-21 | Zu++—TPZ-3 | " | Zn(NO$_3$)$_2$.6H$_2$O |

(C) Various catalysts C were prepared in the same way as in the production of the catalyst B-14 except that various Na+-TPZ-3 zeolites were used as starting materials, as shown in Table 16.

TABLE 16

| Catalyst | $M^{n+}$+Na—TPZ-3 | TPZ-3 | Inorganic salt |
|---|---|---|---|
| C-1 | Na+—TPZ-3 | NaZ-5-1 | — |
| C-2 | Be++—Na+—TPZ-3 | " | Be(NO$_3$)$_2$.3H$_2$O |
| C-3 | Ca++—Na+—TPZ-3 | " | Ca(NO$_3$)$_2$.4H$_2$O |
| C-4 | Sr++—Na+—TPZ-3 | " | Sr(NO$_3$)$_2$ |
| C-5 | Ba++—Na+—TPZ-3 | " | Ba(NO$_3$)$_2$ |
| C-6 | La+++—Na+—TPZ-3 | " | La(NO$_3$)$_3$.6H$_2$O |
| C-7 | Ce+++—Na+—TPZ-3 | " | Ce(NO$_3$)$_3$.6H$_2$O |
| C-8 | Co++—Na+—TPZ-3 | " | Co(NO$_3$)$_2$.6H$_2$O |
| C-9 | Ni++—Na+—TPZ-3 | " | Ni(NO$_3$)$_2$.6H$_2$O |
| C-10 | Cu++—Na+—TPZ-3 | " | Cu(NO$_3$)$_2$.6H$_2$O |
| C-11 | Zn++—Na+—TPZ-3 | " | Zn(NO$_3$)$_2$.6H$_2$O |
| C-12 | Cd++—Na+—TPZ-3 | " | CdCl$_2$ |
| C-13 | Al++—Na+—TPZ-3 | " | Al(NO$_3$)$_3$.9H$_2$O |
| C-14 | Cr++—Na+—TPZ-3 | " | Cr(NO$_3$)$_3$.9H$_2$O |
| C-15 | Mn++—Na+—TPZ-3 | " | Mn(SO$_4$) 7H$_2$O |
| C-16 | Na+—TPZ-3 | NaZ-5-2 | — |
| C-17 | " | -3 | — |

TABLE 16-continued

| Catalyst | $M^{n+}$Na—TPZ-3 | TPZ-3 | Inorganic salt |
|---|---|---|---|
| C-18 | " | -4 | — |

(D) 5.0 g of HZ-5 was suspended in 30 ml of H$_2$O, and then 20 ml of H$_2$O containing 124 mg of Ni(NO$_3$)$_2$.6-H$_2$O was added. With occasional shaking, the mixture was left to stand overnight at 70° C. The solvent was distilled off at about 30° C. under reduced pressure by means of a rotary evaporator. The residue was dried in an electric desiccator at 100° C. for 4 hours, and then calcined in an electric muffle furnace at 450° C. for 8 hours to deposit 0.50% of nickel on H$^+$-TPZ-3.

0.50% Ni-deposited H$^+$-TPZ-3 was mixed with an equal weight of chromatographic alumina gel and the mixture was pelletized to a size of 10 to 20 mesh to give a catalyst D-3.

In the same way as above except that the type of the metal source was changed as shown in Table 17, catalysts D-1 to D-12 were prepared.

TABLE 17

| Catalyst | Amount of metal deposited | TPZ-3 | Metal source |
|---|---|---|---|
| D-1 | 0.50% Fe | HZ-5 | Fe(NO$_3$)$_3$.9H$_2$O |
| D-2 | 0.50% Co | " | Co(NO$_3$)$_2$.6H$_2$O |
| D-3 | 0.50% Ni | " | Ni(NO$_3$)$_2$.6H$_2$O |
| D-4 | 0.47% Rh | " | RhCl$_3$.3H$_2$O |
| D-5 | 0.50% Pd | " | Pd(NH$_4$)$_4$Cl$_2$.H$_2$O |
| D-6 | 0.51% OS | " | OsO$_4$ |
| D-7 | 0.50% Ir | " | IrCl$_4$ |
| D-8 | 0.46% Pt | " | H$_2$PtCl$_6$.6H$_2$O |
| D-9 | 0.50% Re | " | Re$_2$O$_7$ |
| D-10 | 0.50% Cu | " | Cu(NO$_3$)$_2$.6H$_2$O |
| D-11 | 0.50% Zn | " | Zn(NO$_3$)$_2$.6H$_2$O |
| D-12 | 0.30% Pt | " | H$_2$PtCl$_6$.6H$_2$O |

(E) 15.5 g of chromatographic alumina was suspended in 90 ml of H$_2$O, and a portion (10 ml) of 50 ml of an aqueous solution containing 1.028 g of H$_2$PtCl$_6$.6H$_2$O was added. With occasional shaking, they were contacted at 70° C. for 8 hours. Then, the solvent was distilled off at about 30° C. under reduced pressure by means of a rotary evaporator. The residue was dried in an electric desiccator at 100° C. for 6 hours, and then calcined in an electric muffle furnace at 450° C. for 8 hours to deposit 0.50% of Pt on alumina.

The 0.50% Pt-deposited alumina was mixed with an equal weight of HZ-5 and the mixture was pelletized to a size of 10 to 20 mesh to prepare a catalyst E-4.

In the same way as above catalysts E-1 to E-3, and E-5 to E-20 were each prepared except that the type of the metal source and the amount of the metal deposited were changed as shown in Table 18.

In the preparation of the catalysts E-13 to E-16, Sr$^{++}$-Na$^+$-TPZ-3 obtained in C-4 was used, and in the preparation of the catalysts E-17 to E-19, Ba$^{++}$-Na$^+$-TPZ-3 obtained in C-5 was used.

TABLE 18

| Catalyst | M$_1$ on Al$_2$O$_3$ | M$_2^{n+}$—TPZ-3 | TPZ-3 | Al$_2$O$_3$/TPZ-3 (by weight) | Metal source |
|---|---|---|---|---|---|
| E-1 | 0.50% Ni | H$^+$—TPZ-3 | HZ-5 | 1 | Ni(NO$_3$)$_2$.6H$_2$O |
| E-2 | 0.50% Pd | " | " | 1 | Pd(NH$_3$)$_4$-Cl$_2$.H$_2$O |
| E-3 | 0.50% Rh | " | " | 1 | RhCl$_3$.3H$_2$O |
| E-4 | 0.50% Pt | H$^+$—TPZ-3 | HZ-5 | 1 | H$_2$PtCl$_6$.6H$_2$O |
| E-5 | 0.01% Pt | " | " | " | " |
| E-6 | 0.05% Pt | " | " | " | " |
| E-7 | 0.10% Pt | " | " | " | " |
| E-8 | 0.20% Pt | " | " | " | " |
| E-9 | 0.30% Pt | " | " | " | " |
| E-10 | 0.50% Pt | Ne$^+$—TPZ-3 | NaZ-5-1 | " | " |
| E-11 | 0.30% Pt | H$^+$—TPZ-3 | HZ-5 | 2 | " |
| E-12 | 0.30% Pt | " | " | 5 | " |
| E-13 | 0.50% Pt | Sr$^{++}$—Na$^+$—TPZ-3 | NaZ-5-1 | 1 | H$_2$PtCl$_6$.6H$_2$O |
| E-14 | 0.10% Pt | " | " | " | " |
| E-15 | 0.20% Pt | " | " | " | " |
| E-16 | 1.0% Pt | " | " | " | " |
| E-17 | 0.50% Pt | Ba$^{++}$—Na$^+$—TPZ-3 | NaZ-5-1 | 1 | H$_2$PtCl$_6$.6H$_2$O |
| E-18 | 0.10% Pt | " | " | " | " |
| E-19 | 0.20% Pt | " | " | " | " |
| E-20 | 2.0% Pt | H—TPZ-3 | HZ-5 | 1 | " |

(F) Catalysts F-1 to F-9:

(1) Hydrochloric acid (1 ml) and 30 ml of H$_2$O were added to 134 mg of lead chloride, and the mixture was heated at 70° C. to form a solution. To the solution was added 12.8 ml of 50 ml of an aqueous solution containing 1.038 g of H$_2$PtCl$_6$.6H$_2$O. Then, 20 g of chromatographic alumina gel was further added. The mixture was shaken at 70° C. for 2 hours, and the solvent was removed by a rotary evaporator. The residue was dried in an electric desiccator at 100° C. for 4 hours, and calcined in an electric muffle furnace at 450° C. for 8 hours. Nine parts by weight of the resulting alumina having deposited thereon 0.5% Pb and 0.5% Pt was mixed with 1 part by weight of HZ-7, and the mixture was pelletized to a size of 10 to 20 mesh to give a catalyst F-1.

(2) Ten grams of γ-alumina (ACP-1, a product of Catalytic Chemical Co., Ltd.) was suspended in 30 ml of H$_2$O, and a portion (2.66 ml) of 50 ml of an aqueous solution containing 0.998 of H$_2$PtCl$_6$.6H$_2$O was added. Furthermore, a portion (2.87 ml) of 100 ml of an aqueous solution containing 0.905 g of Re$_2$O$_7$ was added. With occasional shaking, the mixture was left to stand overnight. The solvent was distilled off at about 30° C. under reduced pressure by means of a rotary evaporator. The residue was dried in an electric desiccator at 100° C. for 4 hours, and calcined in an electric muffle furnace at 450° C. for 8 hours. Four parts by weight of the resulting alumina having deposited thereon 0.2% of Re and 0.2% Pt was mixed with 1 part by weight of HZ-7 and the mixture was pelletized to a size of 10 to 20 mesh to give a catalyst F-5.

In the same way as in the preparation of the catalyst F-5, catalysts F-2 to F-9 were each prepared except that the type of the metal source, the amount of metal deposited, and the mixing ratio between the metal-deposited alumina and H+-TPZ-3 were changed as shown in Table 19.

The feed xylene mixture contained 0.5% by weight of toluene, 15% by weight of ethylbenzene, 8% by weight of p-xylene and 73.5% by weight of m-xylene and o-

TABLE 19

| Catalyst | $M_1$, $M_2$ on $Al_2O_3$ | $M^{n+}$—TPZ-3 | TPZ-3 | $Al_2O_3$/TPZ-3 (by weight) | Metal source |
|---|---|---|---|---|---|
| F-1 | 0.5% Pt, 0.5% Pb | $H^+$—TPZ-3 | HZ-7 | 9 | $H_2PtCl_6.6H_2O$, $PbCl_2$/HCl |
| F-2 | 0.2% Pt, 0.2% Pd | " | " | 4 | $H_2PtCl_6.6H_2O$, $PdCl_2$/HCl |
| F-3 | 0.2% Pt, 0.2% Ir | " | " | 4 | $H_2PtCl_6.6H_2O$, $IrCl_4$ |
| F-4 | 0.2% Pt, 0.2% Fh | " | " | 4 | $H_2PtCl_6.6H_2O$, $RhCl_3.3H_2O$ |
| F-5 | 0.2% Pt, 0.2% Re | " | " | 4 | $H_2PtCl_6.6H_2O$, $Re_2O_7$ |
| F-6 | 0.2% Pt, 0.2% Os | " | " | 4 | $H_2PtCl_6.6H_2O$, $O_3O_4$ |
| F-7 | 0.5 Pt, 0.5 Re | " | " | 1 | $H_2PtCl_6.6H_2O$, $Re_2O_7$ |
| F-8 | 0.5 Pt, 0.5 Ir | " | " | 1 | $H_2PtCl_6.6H_2O$, $IrCl_4$ |
| F-9 | 0.5 Pt, 0.5 Rh | " | " | 1 | $H_2PtCl_6.6H_2O$, $RhCl_3.3H_2O$ |

(G) 3.5 g of HZ-5 was dipped in 20 ml of an aqueous solution containing 445 mg of $Mg(NO_3)_2.6H_2O$. With occasional stirring, the mixture was left to stand at 70° C. for one day. The solvent was distilled off at about 30° C. under reduced pressure by means of a rotary evaporator. The residue was dried in an electric desiccator at 100° C. for 4 hours, and calcined in an electric muffle furnace at 450° C. for 8 hours. The calcined product was pelletized to a size of 10 to 20 mesh to give 2.0% MgO-deposited TPZ-3 (catalyst G-1).

In the same way as above except that the amount of magnesium nitrate hexahydrate was changed to 1113 mg, 5.0% MgO-deposited TPZ-3 (catalyst G-2) was prepared.

3.5 g of HZ-5 and 70 mg of antimony oxide were kneaded in powdery form and then pelletized to a size of 10 to 20 mesh to give 2.0% $Sb_2O_3$-deposited TPZ-3 (catalyst G-3). In the same way as above except that the amount of antimony oxide was changed to 175 mg, 5.0% $Sb_2O_3$-deposited TPZ-3 (catalyst G-4) was prepared.

PART II: CATALYTIC REACTIONS
II-(1): ISOMERIZATION OF XYLENES
EXAMPLE 30

Each of the catalysts obtained in Example 29 was activated in an electric muffle furnace in an atmosphere of air at 450° C. for 8 hours. 5.0 g of the activated catalyst was filled in a Pyrex glass tube reactor having a diameter of 16 mm and containing a thermocouple inserted therein. The reactor was externally heated by an electric furnace. At each of the reaction temperatures shown in Table 20, a xylene mixture was fed into the reactor under atmospheric pressure and isomerized.

xylene combined.

The results obtained are shown in Table 20.

Figure 8:
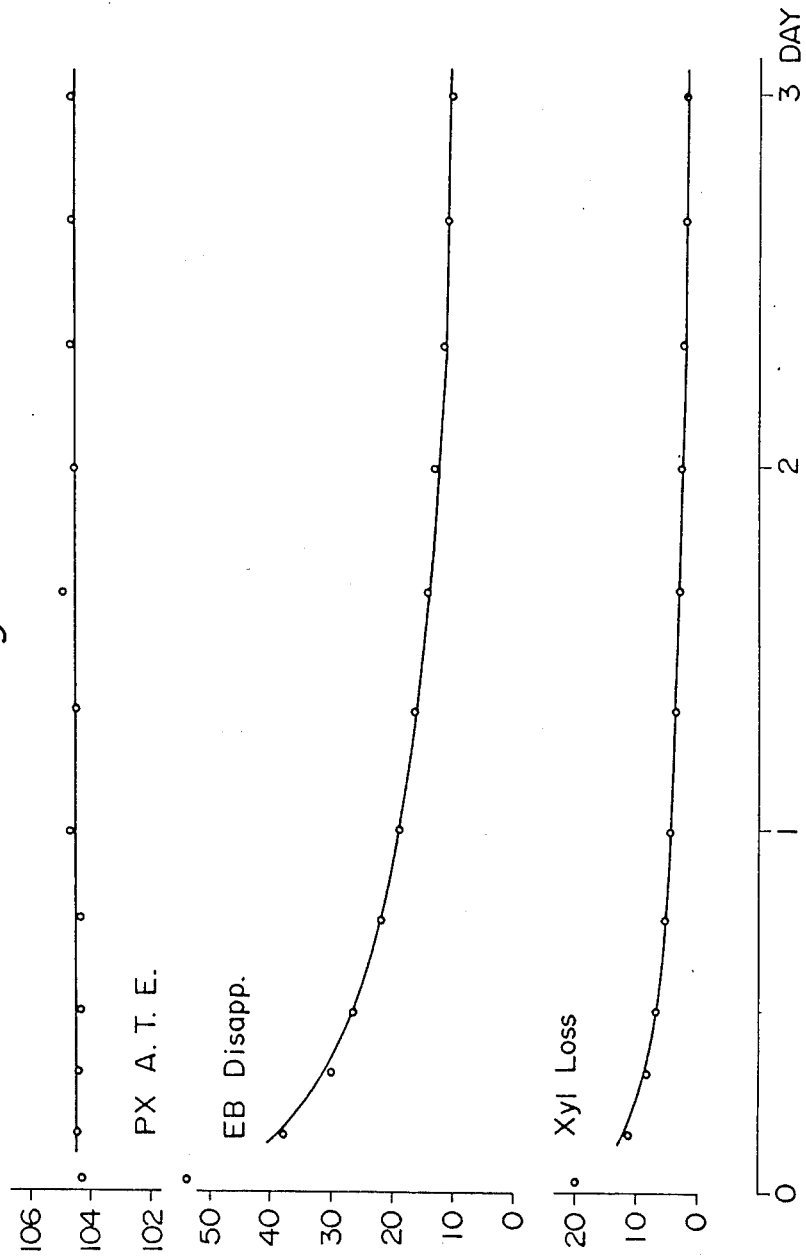
FIG. 8 is a plot of the data for xylene isomerization activity for the crystalline aluminosilicate zeolite of Example 30.

Changes with time of the respective characteristic values obtained with the catalyst A-4 are shown in FIG. 8. FIG. 8 shows that the xylene isomerization activity of the catalyst was very high and its degradation was little even when the feedstock was fed for a long period of time.

In Table 20, the PX approach to equilibrium, the xylene loss and the EB disappearance are defined as follows:

$$PX \text{ approach to equilibrium } (\%) = \frac{\left(\begin{array}{c}PX \text{ concentration in} \\ \text{xylenes in} \\ \text{the product}\end{array}\right) - \left(\begin{array}{c}PX \text{ concentration in the} \\ \text{xylenes in} \\ \text{the feed}\end{array}\right)}{\left(\begin{array}{c}PX \text{ equilibrium} \\ \text{concentration in} \\ \text{xylenes}\end{array}\right) - \left(\begin{array}{c}PX \text{ concentration in} \\ \text{xylenes in} \\ \text{the feed}\end{array}\right)} \times 100$$

$$\text{Xylene loss } (\%) = \frac{\left(\begin{array}{c}\text{Xylene concentration} \\ \text{in the feed}\end{array}\right) - \left(\begin{array}{c}\text{Xylene concentration} \\ \text{in the product}\end{array}\right)}{\text{Xylene concentration in the feed}} \times 100$$

$$EB \text{ disappearance } (\%) = \frac{\left(\begin{array}{c}EB \text{ concentration} \\ \text{in the feed}\end{array}\right) - \left(\begin{array}{c}EB \text{ concentration} \\ \text{in the product}\end{array}\right)}{EB \text{ concentration in the feed}} \times 100$$

In the above equations, the concentrations are in weight percent.

TABLE 20

| Catalyst | Reaction temperature (°C.) | WHSV (hr$^{-1}$) | $H_2$/Hc mole ratio | Feeding time (hours) | PX approach to equilibrium (%) | Xylene loss (%) | EB disappearance (%) |
|---|---|---|---|---|---|---|---|
| A-1 | 430 | 2 | 0 | 24 | 103 | 1.9 | 7.1 |
| A-1 | 430 | 4 | 0 | 24 | 100 | 1.0 | 3.6 |
| A-2 | 430 | 2 | 0 | 24 | 103 | 2.0 | 9.8 |
| A-3 | 430 | 2 | 0 | 24 | 103 | 1.8 | 6.9 |
| A-3 | 430 | 4 | 0 | 24 | 93 | 0.6 | 3.7 |
| A-4 | 430 | 4 | 0 | 24 | 105 | 4.7 | 19.0 |
| A-4 | 430 | 4 | 0 | 48 | 104 | 2.9 | 13.1 |
| A-4 | 430 | 4 | 0 | 72 | 105 | 2.1 | 10.1 |
| A-5 | 430 | 4 | 0 | 48 | 104 | 1.5 | 7.9 |
| A-6 | 430 | 4 | 0 | 48 | 104 | 2.7 | 12.8 |
| A-7 | 430 | 4 | 0 | 48 | 104 | 1.8 | 9.5 |
| B-1 | 350 | 4 | 1 | 48 | 99 | 2.9 | 11.4 |
| B-1 | 375 | 4 | 1 | 48 | 101 | 2.2 | 9.0 |
| B-1 | 400 | 8 | 1 | 48 | 102 | 1.2 | 5.5 |

TABLE 20-continued

| Catalyst | Reaction temperature (°C.) | WHSV (hr$^{-1}$) | H$_2$/Hc mole ratio | Feeding time (hours) | PX approach to equilibrium (%) | Xylene loss (%) | EB disappearance (%) |
|---|---|---|---|---|---|---|---|
| B-1 | 430 | 12 | 1 | 48 | 103 | 1.2 | 5.4 |
| B-2 | 350 | 4 | 1 | 24 | 98 | 2.9 | 11.1 |
| B-3 | 350 | 4 | 1 | 48 | 102 | 4.2 | 14.3 |
| B-4 | 350 | 4 | 1 | 48 | 101 | 4.1 | 13.9 |
| B-5 | 350 | 4 | 1 | 48 | 102 | 4.9 | 16.3 |
| B-6 | 350 | 4 | 1 | 48 | 101 | 3.1 | 11.2 |
| B-7 | 350 | 4 | 1 | 48 | 101 | 3.9 | 13.3 |
| B-8 | 350 | 4 | 1 | 48 | 101 | 3.1 | 11.0 |
| B-9 | 430 | 4 | 1 | 48 | 104 | 3.9 | 14.8 |
| B-10 | 430 | 4 | 1 | 24 | 88.5 | 0.3 | 2.6 |
| B-11 | 430 | 4 | 1 | 48 | 105 | 3.0 | 14.6 |
| B-12 | 430 | 4 | 1 | 48 | 104 | 2.7 | 13.8 |
| B-13 | 430 | 4 | 1 | 48 | 105 | 2.0 | 12.7 |
| B-14 | 430 | 4 | 1 | 48 | 104 | 1.8 | 11.7 |
| B-15 | 430 | 4 | 1 | 48 | 104 | 2.0 | 12.4 |
| B-16 | 430 | 4 | 1 | 48 | 104 | 2.0 | 12.4 |
| B-17 | 430 | 4 | 1 | 48 | 104 | 2.5 | 12.7 |
| B-18 | 430 | 4 | 1 | 48 | 103 | 0.9 | 4.8 |
| B-19 | 430 | 4 | 1 | 48 | 101 | 0.8 | 3.8 |
| B-20 | 430 | 4 | 1 | 48 | 104 | 1.8 | 9.4 |
| B-21 | 430 | 4 | 1 | 48 | 105 | 1.8 | 10.1 |
| C-1 | 430 | 4 | 1 | 48 | 101 | 0.5 | 3.5 |
| C-2 | 430 | 4 | 1 | 48 | 104 | 3.5 | 16.4 |
| C-3 | 430 | 4 | 1 | 48 | 103 | 1.1 | 8.2 |
| C-4 | 430 | 4 | 1 | 48 | 102 | 0.9 | 7.2 |
| C-5 | 430 | 4 | 1 | 48 | 102 | 0.9 | 6.3 |
| C-6 | 430 | 4 | 1 | 48 | 103 | 1.3 | 6.3 |
| C-7 | 430 | 4 | 1 | 48 | 104 | 2.1 | 9.5 |
| C-8 | 430 | 4 | 1 | 48 | 100 | 0.6 | 3.1 |
| C-9 | 430 | 4 | 1 | 48 | 103 | 1.3 | 5.7 |
| C-10 | 430 | 4 | 1 | 48 | 105 | 2.3 | 11.8 |
| C-11 | 430 | 4 | 1 | 48 | 105 | 1.7 | 9.7 |
| C-12 | 430 | 4 | 1 | 48 | 104 | 2.0 | 10.7 |
| C-13 | 430 | 4 | 1 | 48 | 104 | 2.4 | 10.6 |
| C-14 | 430 | 4 | 1 | 48 | 104 | 3.6 | 16.8 |
| C-15 | 430 | 4 | 1 | 48 | 103 | 1.8 | 11.5 |
| C-16 | 430 | 4 | 1 | 48 | 104 | 2.3 | 10.8 |
| C-17 | 430 | 4 | 1 | 48 | 104 | 4.3 | 18.2 |
| C-18 | 430 | 4 | 1 | 48 | 105 | 3.7 | 15.7 |
| D-1 | 430 | 4 | 1 | 48 | 104 | 2.0 | 11.0 |
| D-2 | 430 | 4 | 1 | 48 | 104 | 1.5 | 8.1 |
| D-3 | 430 | 4 | 1 | 48 | 104 | 1.1 | 5.7 |
| D-4 | 430 | 4 | 1 | 48 | 104 | 4.4 | 18.2 |
| D-5 | 430 | 4 | 1 | 48 | 94 | 0.6 | 4.1 |
| D-6 | 430 | 4 | 1 | 48 | 104 | 2.4 | 11.7 |
| D-7 | 430 | 4 | 1 | 48 | 104 | 1.6 | 8.3 |
| D-8 | 430 | 4 | 1 | 48 | 99 | 0.9 | 6.1 |
| D-9 | 430 | 4 | 1 | 48 | 104 | 1.7 | 9.1 |
| D-10 | 430 | 4 | 1 | 48 | 104 | 1.4 | 7.8 |
| D-11 | 430 | 4 | 1 | 48 | 104 | 1.8 | 9.9 |
| D-12 | 430 | 4 | 1 | 48 | 96 | 0.9 | 6.2 |
| E-1 | 430 | 4 | 1 | 48 | 104 | 1.8 | 9.1 |
| E-2 | 430 | 4 | 1 | 48 | 96 | 1.7 | 8.0 |
| E-3 | 430 | 4 | 1 | 48 | 102 | 14.2 | 45.1 |
| E-4 | 430 | 4 | 1 | 48 | 97 | 1.2 | 7.5 |

(*): based on the weight of zeolite

EXAMPLE 31

A xylene mixture was isomerized in the same way as in Example 30 using the catalyst A-5.

Figure 9:
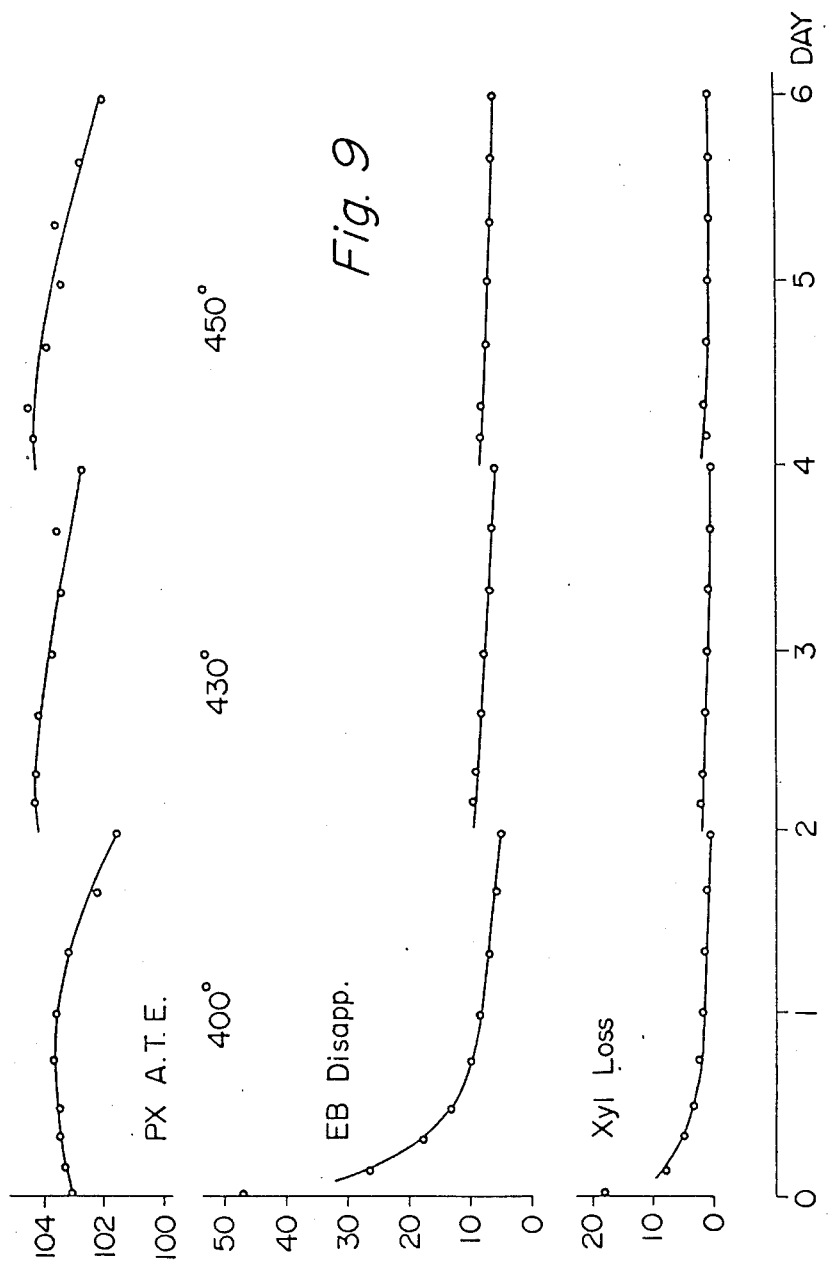
FIG. 9 is a plot of the data for xylene isomerization activity obtained in Example 31.

While maintaining WHSV at 4 hr$^{-1}$, and continuously feeding the xylene mixture without a carrier hydrogen gas, the temperature was raised successively to 400° C., 430° C., and 450° C. This was continued for 6 days. The results are shown in FIG. 9. It is seen from FIG. 9 that the very high xylene isomerizing activity was maintained, and this could be increased further by successively increasing the temperature. During this time, the disproportionating activity and the transalkylating activity of the catalyst were maintained at a low level, and under the aforesaid conditions, these activities did not appreciably increase by raising of the temperature.

EXAMPLE 32

Using the catalyst A-2, a xylene mixture was isomerized without a carrier hydrogen gas in the same way as in Example 30. For the first 9 hours, a xylene mixture containing 1% of propylamine was fed, and thereafter, a xylene mixture not containing the amine was fed. The results obtained after the lapse of 13 hours are shown in Table 21 together with the results of a comparison in which such a treatment was not performed.

TABLE 21

|  | After passing the amine | Comparison |
|---|---|---|
| Xylene feeding time (hours) | 18 | 18 |
| Temperature (°C.) | 430 | 430 |
| WHSV (hr$^{-1}$)* | 2 | 2 |
| PX approach to equilibrium (%) | 98 | 103 |
| Xylene loss (%) | 0.5 | 2.8 |
| EB disappearance (%) | 3.6 | 12.1 |

*based on the weight of zeolite

It is assumed that by affecting a part of the acidic site of the catalyst by treatment with an amine, the disproportionating and transalkylating activities of the catalyst can be reduced without a substantial decline in its xylene isomerizing activity.

EXAMPLE 33

The catalyst A-5 was treated with steam for 48 hours at 500° C. and a WHSV of 0.44 hr$^{-1}$ by using air as a carrier gas. Using the steam-treated catalyst, xylenes were isomerized without a carrier hydrogen gas. The results are shown in Table 22 together with those obtained without performing the steaming treatment (comparison).

It is seen that by the steaming treatment, the disproportionating and transalkylating activities of the catalyst can be reduced without a substantial decline in its xylene isomerizing activity.

TABLE 22

|  | Steaming | Comparison |
|---|---|---|
| Xylene feeding time (hours) | 24 | 24 |
| Temperature (°C.) | 430 | 430 |
| WHSV (hr$^{-1}$)* | 4 | 4 |
| PX approach to equilibrium (%) | 99.0 | 104.5 |
| Xylene loss (%) | 0.8 | 2.6 |
| EB disappearance (%) | 4.8 | 12.4 |

*based on the weight of zeolite

EXAMPLE 34

The catalyst D-5 was filled in a fixed bed reactor, and under hydrogen pressure, xylenes are isomerized in the gaseous phase. The results are shown in Table 23. It is seen that even under very mild conditions, the catalyst had high xylene isomerizing activity and its deterioration was not observed over a long period of time.

TABLE 23

| Feeding time (hrs) | Temperature (°C.) | WHSV (*) (hr$^{-1}$) | Pressure (psi) | H$_2$/xylenes mole ratio | PX approach to equilibrium (%) | Xylene loss (%) | EB disappearance (%) |
|---|---|---|---|---|---|---|---|
| 105 | 430 | 8 | 90 | 2 | 104 | 5.6 | 19.0 |
| 157 | 380 | 4 | 150 | 2 | 103 | 4.1 | 11.9 |
| 225 | 350 | 4 | 150 | 2 | 101 | 1.5 | 4.8 |
| 268 | 350 | 4 | 150 | 5 | 101 | 1.2 | 3.7 |
| 313 | 350 | 4 | 150 | 9 | 102 | 0.9 | 3.4 |
| 381 | 350 | 8 | 150 | 5 | 98 | 0.7 | 2.3 |
| 407 | 430 | 16 | 150 | 5 | 104 | 4.0 | 15.7 |
| 419 | 320 | 4 | 150 | 5 | 93 | 0.6 | 2.3 |
| 430 | 400 | 16 | 150 | 5 | 103 | 2.0 | 7.4 |
| 457 | 400 | 8 | 150 | 5 | 103 | 4.0 | 13.9 |

(*): based on the weight of zeolite

II-(2): ISOMERIZATION OF ETHYLBENZENE TO XYLENES

EXAMPLE 25

Each of the Pt-type catalysts obtained in Example 29 was filled in a pressure flow reactor of the fixed bed type, and under hydrogen pressure, ethylbenzene was fed and isomerized to xylenes in the gaseous phase. Prior to this reaction, each of the catalysts had been subjected to a reducing treatment in a stream of hydrogen at 430° to 480° C. under atmospheric pressure for 4 hours. The results are shown in Table 24.

It is seen that the yield of C$_8$ hydrocarbons (aromatics + naphthenes) was very high, and the selectivity for xylenes was good. Among the non-aromatic components, the percentage of C$_8$ naphthenes formed was high. This shows that cracking of C$_8$ naphthenes did not easily take place.

In Table 24, EB which disappeared, xylenes formed and C$_8$ naphthenes formed are shown in weight per 100 g of EB fed.

In the table, C$_8$N stands for C$_8$ naphthenes; C$_8$A+N, C$_8$ aromatics + C$_8$ naphthenes; and NA, non-aromatics.

TABLE 24

| Catalyst | E-4 | E-4 | E-12 | E-4 | E-20 | E-10 | E-13 | D-8 | E-16 |
|---|---|---|---|---|---|---|---|---|---|
| Temperature (°C.) | 350 | 400 | 430 | 315 | 370 | 430 | 430 | 350 | 400 |
| WHSV (*) (hr$^{-1}$) | 5 | 20 | 30 | 3 | 10 | 10 | 10 | 5 | 3 |
| Pressure (psi) | 100 | 200 | 200 | 30 | 80 | 250 | 200 | 100 | 150 |
| H$_2$/HC mole ratio | 4.86 | 7.40 | 6.87 | 3.32 | 6.93 | 7.73 | 7.47 | 6.00 | 6.71 |
| EB disappearance (%) | 55.07 | 51.95 | 40.61 | 19.88 | 38.82 | 26.07 | 22.70 | 16.17 | 40.62 |
| Xylene formed (%) | 18.85 | 22.68 | 18.23 | 4.91 | 21.15 | 11.52 | 10.39 | 2.14 | 22.29 |
| C$_8$N formed (%) | 33.53 | 17.44 | 5.42 | 8.83 | 9.29 | 10.50 | 6.76 | 5.90 | 11.23 |
| Yield of C$_8$AR + N (mole %) | 95.50 | 87.22 | 82.85 | 93.43 | 91.23 | 95.46 | 94.14 | 91.59 | 92.14 |
| ΔXyl/ΔEB-ΔC$_8$N (weight ratio) | 85.83 | 65.72 | 51.80 | 44.44 | 71.63 | 79.18 | 65.18 | 20.88 | 75.85 |
| ΔC$_8$N/ΔNA (weight ratio) | 93.78 | 68.76 | 42.73 | 94.03 | 75.79 | 82.59 | 77.56 | 80.59 | 77.62 |

(*): based on the weight of zeolite

EXAMPLE 36

A xylene mixture was fed and isomerized in the presence of the E-20 catalyst in the same way as in Example 35. The results are shown in Table 25. It is seen that isomerization of ethylbenzene to xylenes took place very effectively, and the p-xylene approach to equilibrium was high.

TABLE 25

| Catalyst | (Feed) gr. | E-20 (Product) gr. |
| --- | --- | --- |
| NA total | 6.90 | 8.41 |
| $C_8N$ | 6.78 | 6.52 |
| B | 0.14 | 0.30 |
| T | 1.85 | 2.13 |
| EB | 15.49 | 10.80 |
| PX | 7.76 | 18.55 |
| MX | 48.70 | 41.41 |
| OX | 19.09 | 17.52 |
| $C_9{}^+Ar$ | 0.07 | 1.00 |
| Feeding time (hrs) | | 265 |
| WHSV*($hr^{-1}$) | | 10 |
| Temperature (°C.) | | 370 |
| Total pressure (psia) | | 80 |
| $H_2$/HC mole ratio | | 6.91 |
| PX approach to equilibrium (%) | | 102.28 |
| EB disappearance (%) | | 30.27 |
| Xylene loss (%) | | −2.56 |
| Total yield of $C_8A + N$ (%) | | 96.92 |

*based on the weight of zeolite

II-(3): DISPROPORTIONATION OF TOLUENE

EXAMPLE 27

Each of the catalysts A-4 and A-5 was calcined at 450° C. for 8 hours in an electric muffle furnace in an atmosphere of air, and filled in a Pyrex glass tube reactor. Toluene was disproportionated therein in the gaseous phase under atmospheric pressure in the absence of a carrier gas. The reaction conditions are shown in Table 26.

The results are also shown in Table 26.

COMPARATIVE EXAMPLE 1

Ferrierite and ZSM-5 zeolite were synthesized in accordance with British Patent Application No. 11844/74 and U.S. Pat. No. 3,965,207, respectively. Using each of these zeolites, toluene was disproportionated in the same way as in Example 37.

Furthermore, the same disproportionation reaction of toluene was performed in the presence of commercial mordenite (Zeolon 900H). The results are shown in Table 26 together with the results obtained in Example 37.

It is seen that TPZ-3 zeolites show a high toluene conversion at relatively low temperatures to high temperatures as compared with the other zeolites.

TABLE 26

| | Zeolite | Temperature (°C.) | WHSV ($hr^{-1}$) | Feeding time (hrs) | Toluene conversion (%) |
| --- | --- | --- | --- | --- | --- |
| Example 37 | TPZ-3 catalyst (A-4) | 300 | 0.93 | 0.5–1.5 | 35.71 |
| | | 350 | 0.92 | 0.5–1.5 | 45.87 |
| | | 500 | 1.00 | 0.5–1.5 | 44.04 |
| | TPZ-3 catalyst (A-5) | 350 | 2.14 | 1–2 | 41.26 |
| | | 400 | 1.94 | 1–2 | 43.67 |
| | | 450 | 2.03 | 1–2 | 32.43 |
| Comparative Example 1 | Mordenite (Zeolon 900 H) | 300 | 0.63 | 0–1 | 29.66 |
| | | 350 | 0.63 | 0–1 | 38.01 |
| | | 400 | 0.63 | 0–1 | 30.14 |
| | Ferrierite | 350 | 0.63 | 0–1 | 8.11 |
| | | 450 | 0.63 | 0–1 | 18.21 |
| | | 550 | 0.63 | 0–1 | 24.95 |
| | ZSM-5 zeolite | 350 | 0.63 | 0–1 | 4.75 |
| | | 400 | 0.63 | 0–1 | 15.70 |
| | | 550 | 3.50 | 0–1 | 44.74 |

EXAMPLE 28

In the same way as in Example 37, toluene was disproportionated in the presence of the catalyst A-5. The results are shown in Table 27 together with those obtained with mordenite (Zeolon 900H).

TABLE 27

| Zeolite | Temperature (°C.) | WHSV ($hr^{-1}$) | Feeding time (hrs) | Toluene conversion (%) |
| --- | --- | --- | --- | --- |
| TPZ-3 (catalyst A-5) | 350 | 2.14 | 1–2 | 41.26 |
| | 350 | 2.14 | 3–4 | 38.01 |
| | 350 | 2.14 | 6–7 | 26.18 |
| Mordenite (zeolon 900 H) | 350 | 0.63 | 0–1 | 38.01 |
| | 350 | 0.63 | 1–2 | 20.86 |
| | 350 | 0.63 | 2–3 | 11.75 |
| | 350 | 0.63 | 3–4 | 7.80 |

It is seen from the results obtained that in spite of the absence of a carrier gas and the large amount of the feedstock, TPZ-3 exhibited very stable catalytic performance.

EXAMPLE 39

Using the catalyst obtained in Example 29, toluene and 1,2,4-trimethylbenzene were subjected to transalkylation reaction in the same way as in Example 37. The feed had a toluene/1,2,4-trimethylbenzene (TMB) molar ratio of 1. It was fed at a WHSV of 2 $hr^{-1}$ (based on the weight of zeolite). The results obtained between 1 and 2 hours from the start of feeding are shown in Table 28.

TABLE 28

| Catalyst | Temperature (°C.) | $H_2$/Hydrocarbon (mole ratio) | Toluene conversion (%) | TBM conversion (%) | Yield of benzene (mole %) | Yield of xylenes (mole %) |
| --- | --- | --- | --- | --- | --- | --- |
| A-5 | 350 | 0 | 39.3 | 34.9 | 13.5 | 83.1 |
| A-5 | 400 | 0 | 42.0 | 38.6 | 13.2 | 81.6 |
| A-5 | 450 | 0 | 31.7 | 35.1 | 14.2 | 78.4 |
| B-12 | 450 | 2 | 34.6 | 32.8 | 12.0 | 79.0 |

EXAMPLE 40

Each of the catalysts shown in Table 29 was filled in a Pyrex glass tube reactor after it had been activated in an electric muffle furnace in an air atmosphere at 450° C. for 8 hours. While passing hydrogen (hydrogen/toluene=2) as a carrier gas, toluene was disproportionated in the gaseous phase at 450° C. at a WHSV of 2 hr$^{-1}$ (based on the weight of zeolite under atmospheric pressure. The results obtained between 1 hour and 3 hours after the initiation of feeding are shown in Table 29.

It is seen that the catalyst showed a high conversion at low pressures, and scarcely any deterioration in catalytic activity was noted under low hydrogen partial pressures.

TABLE 30

| Feeding (hrs) | Temperature (°C.) | Pressure (psi) | H$_2$/toulene mole ratio | Toluene conversion (%) | Yield of benzene (mole %) | Yield of xylene (mole %) |
|---|---|---|---|---|---|---|
| 111 | 450 | 150 | 4.0 | 25.5 | 49.7 | 47.5 |
| 150 | 500 | 150 | 4.1 | 38.7 | 53.1 | 43.4 |
| 99 | 400 | 400 | 0.9 | 37.3 | 62.2 | 23.0 |
| 149 | 450 | 400 | 2.0 | 46.7 | 68.1 | 30.3 |

TABLE 31

| Feeding Time (hrs) | Temperature (°C.) | Pressure (psi) | H$_2$/toluene plus TMB mole ratio | Toluene conversion (%) | TMB conversion (%) | Yield of benzene (mole %) | Yield of xylenes (mole %) |
|---|---|---|---|---|---|---|---|
| 290 | 450 | 150 | 3.4 | 25.2 | 33.9 | 12.2 | 78.2 |
| 51 | 400 | 250 | 4.5 | 24.4 | 31.0 | 12.7 | 75.9 |
| 214 | 450 | 400 | 1.0 | 33.1 | 41.7 | 20.4 | 75.6 |

TABLE 29

| Catalyst | Toluene conversion (%) | Yield of benzene (mole %) | Yield of xylenes (mole %) |
|---|---|---|---|
| B-1 | 40.8 | 51.6 | 44.8 |
| B-11 | 37.5 | 49.9 | 46.5 |
| B-12 | 35.6 | 50.0 | 46.7 |
| B-13 | 18.4 | 49.4 | 49.1 |
| B-14 | 17.6 | 49.3 | 49.0 |
| B-15 | 10.6 | 48.7 | 50.3 |
| B-16 | 38.9 | 50.4 | 46.0 |
| B-17 | 38.4 | 50.2 | 46.3 |
| D-1 | 37.8 | 50.9 | 45.7 |
| D-2 | 32.5 | 50.6 | 46.6 |
| D-3 | 28.5 | 51.0 | 46.8 |
| D-5 | 25.7 | 50.8 | 47.6 |
| D-6 | 37.9 | 50.1 | 46.6 |
| D-7 | 39.7 | 51.4 | 44.9 |
| D-8 | 40.1 | 51.9 | 44.9 |
| D-9 | 39.7 | 50.8 | 45.9 |
| D-10 | 36.0 | 50.7 | 46.1 |
| D-11 | 30.7 | 50.5 | 46.8 |

EXAMPLE 41

The catalyst D-5 was activated in an electric muffle furnace in an atmosphere of air at 450° C. for 8 hours, and filled in a fixed bed reactor. Under hydrogen pressure, toluene or an equimolar mixture of toluene and 1,2,4-trimethylbenzene was fed into the reactor in the gaseous phase at a WHSV of 2 hr$^{-1}$ (based on the weight of zeolite) to perform the disproportionation or transalkylation of toluene. The results are shown in Tables 30 and 31 respectively.

II-(4): METHYLATION OF TOLUENE

EXAMPLE 42

The catalyst A-5 was activated in an electric muffle furnace in an atmosphere of air at 450° C. for 8 hours, and filled in a Pyrex glass tube reactor. A mixture of toluene and methanol (1:1 by mole) was fed into the reactor under atmospheric pressure in the gaseous phase in the absence of a carrier gas to alkylate toluene. The results are shown in Table 32.

COMPARATIVE EXAMPLE 2

Zeolite ZSM-5 was synthesized in accordance with the method of U.S. Pat. No. 3,965,207. Toluene was alkylated with methanol in the same way as in Example 42 using the zeolite ZSM-5. The results are shown in Table 32.

In Example 42 and Comparative Example 2, the reaction temperature was 500° C., and WHSV was 5 hr$^{-1}$.

It is seen that TPZ-3 showed very high activity and low activity loss in the alkylation reaction of toluene with methanol despite the absence of a carrier gas, and that as a result of the degradation of the catalyst, the proportion of o-xylene in the three xylene isomers increased. This tendency is not seen in ZSM-5.

TABLE 32

| Catalyst | Feeding time (hrs) | Toluene conversion (%) | Xylene yield (%) | Yield of methanol (%) | PX concentration in xylenes (%) | OX concentration in xylenes (%) |
|---|---|---|---|---|---|---|
| A-5 | 0.5–1.5 | 51.5 | 60.3 | 68 | 23.3 | 25.6 |
|  | 2.5–3.5 | 39.5 | 67.5 | 52 | 19.4 | 40.9 |
|  | 5.5–6.5 | 18.5 | 79.9 | 22 | 21.3 | 50.5 |
| Comparative Example 2 | 0.5–1.5 | 47.2 | 78.3 | 48 | 24.0 | 23.9 |
|  | 3.5–4.5 | 38.7 | 75.1 | 46 | 27.8 | 21.9 |
|  | 5.5–6.5 | 23.3 | 72.4 | 40 | 35.7 | 25.0 |

EXAMPLE 43

Using each of the TPZ-3 zeolite catalysts having various metal oxide deposited thereon (G-series catalysts obtained in Example 29), toluene was alkylated with methanol in the same way as in Example 42. The results are shown in Table 33.

TABLE 33

| Catalyst | Feeding time (hrs) | Toluene conversion (%) | Yield of xylenes (%) | Yield of methanol (%) | PX concentration in the xylenes (%) | OX concentration in the xylenes (%) |
|---|---|---|---|---|---|---|
| G-1 | 2.5-3 | 41.2 | 68.0 | 54 | 18.8 | 42.1 |
| G-2 | 0.5-1 | 36.1 | 70.8 | 46 | 19.9 | 42.8 |
| G-3 | 2.5-3 | 34.5 | 73.9 | 43 | 18.2 | 48.9 |
| G-4 | 0.5-1 | 36.4 | 73.6 | 45 | 19.4 | 45.2 |

II-(5): OTHER REACTIONS

EXAMPLE 44

The catalyst A-2 was activated in an electric muffle furnace in an atmosphere of air at 450° C. for 8 hours, and then filled in a Pyrex glass tube reactor. Methanol was passed through the reactor under atmospheric pressure at 500° C. and a WHSV of 5 $hr^{-1}$. The organic products obtained during a period of 3 hours from the start of feeding were analyzed. The results are shown in Table 34.

TABLE 34

| Analysis of gas (wt. %) | | Analysis of liquid (wt. %) | |
|---|---|---|---|
| $C_1$ | 67.3 | $Co+N.A.$ | 15.0 |
| $C_2$ | 6.3 | B | 0.5 |
| $C_3$ | 12.9 | T | 3.2 |
| $C_4$ | 5.4 | X | 13.0 |
| $C_5$ | 8.1 | $Ca+Ar$ | 68.3 |
| Total | 100 | Total | 100 |

EXAMPLE 45

The catalyst E-3 was activated in an electric muffle furnace in an air atmosphere at 450° C. for 8 hours, and filled in a Pyrex glass tube reactor. The catalyst was further subjected to reducing treatment with hydrogen at 450° C. and atmospheric pressure for 4 hours, and then adjusted to the reaction temperature. Toluene was passed through the reactor under atmospheric pressure in the presence of hydrogen as a carrier gas to dealkylate it. The results are shown in Table 35. As a comparison, the results with a 0.5% Rh-deposited alumina catalyst not containing TPZ-3 are also shown in Table 35.

TABLE 35

| Catalyst | Temperature (°C.) | WHSV ($hr^{-1}$) | $H_2$/toluene mole ratio | Toluene conversion (%) | Benzene selectivity (%) | Xylene selectivity (%) | $C_9+Ar$ selectivity (%) |
|---|---|---|---|---|---|---|---|
| E-3 | 350 | 1.9 | 2.0 | 27.6 | 58.1 | 35.2 | 2.0 |
| E-3 | 400 | 2.0 | 5.2 | 47.2 | 81.8 | 6.0 | 0.1 |
| E-3 | 450 | 1.9 | 5.1 | 76.0 | 68.3 | 2.0 | 0.1 |
| 0.5% Rh/$Al_2O_3$ | 450 | 1.9 | 2.0 | 36.9 | 76.9 | 6.9 | 0.3 |

The selectivities shown in Table 35 are the percentages of the amount in moles of the respective products based on one mole of toluene which disappeared.

EXAMPLE 46

Each of the catalysts shown in Table 36 was calcined in an electric muffle furnace in an air atmosphere at 450° C. for 8 hours, and then filled in a Pyrex glass tube reactor. A saturated gas stream (the pressure of hexane=0.2 atm.) obtained by passing nitrogen gas through hexanes at 25° C. placed in an absorbing bottle was supplied to the catalyst bed of the reactor. The reaction temperature was controlled so as to provide a hexane conversion of 5 to 40%, where it is understood that the hexanes fed are $C_6$-paraffins containing at least 80% of n-hexane. The conversion of hexanes is defined as shown below.

$$\text{Hexane conversion } (\epsilon) = 1 - \left( \frac{\text{Concentration (\%) of hexanes in the product}}{100} \right)$$

The product obtained between 10 minutes to 20 minutes after the starting of feeding was sampled, and analyzed by gas chromatography.

The reaction velocity constant at each of the reaction temperatures is calculated as follows:

$$k = (1/\tau) \, ln \, \frac{1}{1 - \epsilon}$$

wherein k is the velocity constant in $sec^{-1}$, $\tau$ is the contact time in seconds [the volume of the catalyst (ml)/the velocity of the feed gas (ml/sec)], and $\epsilon$ is the conversion of hexanes.

The above conversion of hexanes was achieved at a reaction temperature of 150° to 550° C. with a contact time of 1 to 20 seconds.

The cracking indices of the catalysts, expressed in terms of a temperature at which the reaction velocity constant became 0.5, are shown in Table 36.

TABLE 36

| Catalyst | TPZ-3 | Cracking index |
|---|---|---|
| A-5 | H—TPZ-3 | 260-280 |
| C-1 | Na—TPZ-3 | 500-550 |
| C-2 | Be—Na—TPZ-3 | 300-320 |
| C-16 | Na—TPZ-3 | 290-310 |
| C-17 | Na—TPZ-3 | 310-330 |
| C-18 | Na—TPZ-3 | 380-400 |
| B-9 | Li—H—TPZ-3 | 320-340 |
| B-10 | K—H—TPZ-3 | 500-520 |
| C-4 | Sr—Na—TPZ-3 | 400-420 |
| C-6 | La—Na—TPZ-3 | 450-470 |
| — | H—ZSM-5* | <260 |
| N-631-NH** | Silica-alumina | >450 |

*Obtained in the comparative comparison of Example 27.
**A product of Nikki Chemicals, Co., Ltd.

EXAMPLE 47

Each of the catalysts shown in Table 37 was activated in an electric muffle furnace in an air atmosphere at 450° C. for 8 hours, and filled in a Pyrex glass tube reactor. Benzene and cyclohexane were subjected to hydrogenation-dehydrogen reactions and isomerization reaction of the sketeton of naphthenes. Prior to the reactions, the catalyst was treated in hydrogen at 450° C. under atmospheric pressure for 2 hours. The reactions were carried out at 300° C. and a WHSV of 2.5 hr$^{-1}$ (based on the entire catalyst weight) under atmospheric pressure. The hydrogen/hydrocarbon mole ratio was maintained at 6. The results are shown in Table 37.

It is seen that the skeletal isomerization of naphthene took place effectively, and the loss of $C_6$ naphthenes was very small.

In the table, Na represents non-aromatic components; $C_6N$, $C_6$ naphthenese; and MCP, methylcyclopentane.

TABLE 37

| Cat-a-lyst | Benzene Feed | | | Cyclohexane Feed | | |
|---|---|---|---|---|---|---|
| | ΔNA | MCP/C$_6$N | C$_6$N/NA | ΔNA | MCP/C$_6$N | C$_6$N/NA |
| E-4 | 9.8 | 53.9 | 98.3 | 66.6 | 53.2 | 96.8 |
| E-5 | 0.2 | 76.3 | 86.0 | 1.3 | 31.1 | 98.8 |
| E-6 | 1.7 | 58.9 | 96.3 | 5.1 | 33.5 | 98.6 |
| E-7 | 3.1 | 56.5 | 97.2 | 11.5 | 36.7 | 98.4 |
| E-8 | 6.8 | 53.7 | 98.2 | 30.6 | 42.7 | 98.2 |
| E-9 | 8.0 | 53.1 | 98.1 | 47.1 | 45.6 | 98.0 |
| E-10 | 6.0 | 3.5 | 99.7 | 92.5 | 9.3 | 99.4 |
| E-11 | 7.6 | 50.1 | 99.1 | 64.9 | 45.9 | 99.0 |
| E-12 | 7.6 | 32.2 | 99.6 | 75.9 | 37.7 | 99.6 |
| E-13 | 6.6 | 11.0 | 99.6 | 94.3 | 18.9 | 99.2 |
| E-14 | 6.7 | 12.9 | 99.3 | 73.0 | 25.6 | 99.7 |
| E-15 | 5.8 | 12.3 | 99.6 | 48.4 | 26.9 | 99.7 |
| E-17 | 6.3 | 2.8 | 99.5 | 92.0 | 5.4 | 99.3 |
| E-18 | 5.6 | 3.7 | 99.7 | 59.4 | 6.2 | 99.8 |
| E-19 | 6.2 | 5.7 | 99.4 | 74.9 | 10.9 | 99.7 |
| F-1 | 4.4 | 12.2 | 99.5 | 28.1 | 16.5 | 99.7 |
| F-2 | 1.4 | 50.0 | 94.8 | 8.1 | 33.2 | 98.8 |
| F-3 | 2.9 | 47.0 | 99.1 | 4.4 | 31.6 | 98.7 |
| F-4 | 1.9 | 47.9 | 98.6 | 4.1 | 30.3 | 98.6 |
| F-5 | 4.3 | 52.3 | 99.0 | 21.7 | 36.7 | 99.0 |
| F-6 | 3.7 | 49.6 | 98.9 | 18.1 | 36.0 | 98.9 |

EXAMPLE 48

In the same way as in Example 47, methylcyclopentane was fed and converted to benzene.

The results are shown in Table 38. It is seen that the conversion of $C_6$ naphthenes was high, and the selectivity of the catalyst for benzene was very high. Furthermore, the hydrogenolysis of $C_6$ naphthenes was kept at a low level.

In the Table, Ar represents aromatic components; and $C_5^-$, the sum of $C_1$ to $C_5$ hydrocarbons, shown by the mole ratios of the starting material converted to the individual components.

TABLE 38

| Catalyst | Temperature (°C.) | WHSV* (hr$^{-1}$) | H$_2$/HC mole ratio | Time (hrs) | Mole ratios (%) | | | |
|---|---|---|---|---|---|---|---|---|
| | | | | | ΔC$_6$N | ΔC$_5^-$/ΔC$_6$N | ΔBz/ΔC$_6$N | ΔAr/ΔC$_6$N |
| F-2 | 430 | 2.50 | 2.61 | 1–3 | 76.3 | 3.1 | 84.9 | 93.7 |
| F-3 | 430 | 4.42 | 3.12 | 1–3 | 80.8 | 2.4 | 85.4 | 89.9 |
| F-4 | 430 | 4.71 | 4.11 | 1–3 | 41.2 | 3.4 | 72.8 | 79.2 |
| F-5 | 430 | 4.54 | 3.14 | 1–3 | 50.6 | 4.3 | 76.1 | 84.8 |
| F-6 | 430 | 4.61 | 3.03 | 1–3 | 75.9 | 2.4 | 86.4 | 89.9 |
| E-10 | 430 | 5.08 | 3.15 | 1–3 | 19.9 | 8.5 | 38.8 | 42.1 |
| E-4 | 430 | 5.10 | 3.07 | 1–3 | 19.1 | 13.7 | 37.1 | 50.0 |
| E-16 | 430 | 5.03 | 3.05 | 1–3 | 31.0 | 6.9 | 53.6 | 57.5 |
| F-7 | 430 | 5.32 | 2.84 | 1–3 | 43.0 | 4.6 | 75.6 | 82.1 |
| F-8 | 430 | 5.01 | 3.15 | 1–3 | 32.5 | 5.5 | 64.9 | 71.8 |
| F-9 | 430 | 5.18 | 3.01 | 1–3 | 25.2 | 6.2 | 53.3 | 60.0 |

*based on the entire catalyst weight

What we claim is:

1. In a process for isomerizing xylenes and ethylbenzene which comprises contacting an aromatic hydrocarbon stock mainly containing xylene isomers and ethylbenzene, in which the concentration of at least one xylene isomer is lower than the thermodynamical equilibrium concentration with a catalyst composition at an elevated temperature in the vapor phase in the presence of hydrogen, the improvement which comprises using as the catalyst composition a catalyst composition containing as catalytically active components (A) alumina having deposited thereon platinum or its oxide, and (B) a crystalline aluminosilicate zeolite characterized by having a composition of the following general formula expressed in terms of the mole ratios of oxides in the anhydrous state $$xM_{2/n}O \cdot Al_2O_3 \cdot ySiO_2 \qquad (I)$$

where M represents at least one cation having a valence of n selected from the group consisting of a hydrogen ion and metal cations of metals of Group IA, IIA and IIIB of the periodic table, x is a number between 0.5 and 4, and y is a number of at least 10, and having an X-ray diffraction pattern showing at least the following significant peaks

| Interplanar spacing d(Å) | Relative intensity |
|---|---|
| 11.2 ± 0.5 | medium to strong |
| 9.9 ± 0.5 | medium to strong |
| 4.67 ± 0.1 | medium |
| 4.33 ± 0.1 | very strong |
| 4.02 ± 0.05 | strong to very strong |
| 3.83 ± 0.05 | medium |
| 3.72 ± 0.05 | weak to medium |
| 3.44 ± 0.04 | weak to strong |
| 3.33 ± 0.04 | weak to strong |
| 3.28 ± 0.03 | medium |

2. The process of claim 1 wherein the aromatic hydrocarbon stock further contains a non-aromatic hydrocarbon.

3. The process of claim 1 wherein the temperature is in the range of 280° to 500° C.

4. The process of claim 1 wherein the contact is carried out at a weight hourly space velocity of 0.1 to 200/hour.

5. The process of claim 1 wherein the contact is carried out under a pressure of from atmospheric pressure to 30 kg/cm$^2$/G.

6. The process of claim 1 wherein the amount of hydrogen is 1 to 20 moles per mole of the entire hydrocarbon in the stock.

7. The process of claim 1 wherein M in the formula (I) is a hydrogen ion.

8. The process of claim 1 wherein M in formula (I) is a metal of group IA, IIA or IIIB of the periodic table.

9. The process of claim 1 wherein x in the formula (I) is a number between 0.9 and 3.

10. The process of claim 1 wherein y in formula (I) is a number in the range of 10 to 2000.

11. The process of claim 1 wherein y in the formula (I) is a number in the range from 10 to 500.

12. The process of claim 1 wherein the catalytically active component (A) of the catalyst composition in alumina having deposited thereon platinum or its oxide together with another catalytically active metal or metal oxide selected from the group consisting of lead, palladium, iridium, rhodium, rhenium, osmium and the oxides thereof.

* * * * *